(12) United States Patent
Gerritsen et al.

(10) Patent No.: US 7,572,447 B2
(45) Date of Patent: Aug. 11, 2009

(54) METHODS AND COMPOSITIONS FOR SELECTIVE MODULATION OF VASCULARIZATION

(75) Inventors: Mary E. Gerritsen, San Mateo, CA (US); Jo-Anne S. Hongo, Redwood City, CA (US); Constance H. Zlot, Kentfield, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/046,795

(22) Filed: Mar. 12, 2008

(65) Prior Publication Data

US 2008/0241159 A1 Oct. 2, 2008

Related U.S. Application Data

(63) Continuation of application No. 10/824,075, filed on Apr. 14, 2004, now Pat. No. 7,407,660.

(60) Provisional application No. 60/463,226, filed on Apr. 16, 2003.

(51) Int. Cl.
 *A61K 39/395* (2006.01)
 *C12N 5/12* (2006.01)
 *C12P 21/08* (2006.01)

(52) U.S. Cl. ............... 424/145.1; 424/178.1; 435/326; 530/388.24

(58) Field of Classification Search ..................... None
See application file for complete search history.

(56) References Cited

U.S. PATENT DOCUMENTS

| | | | |
|---|---|---|---|
| 5,468,634 | A | 11/1995 | Liu |
| 5,547,856 | A | 8/1996 | Godowski et al. |
| 5,733,876 | A | 3/1998 | O'Reilly et al. |
| 5,871,697 | A | 2/1999 | Rothberg et al. |
| 6,099,841 | A | 8/2000 | Hillan et al. |
| 6,365,572 | B1 | 4/2002 | Stilz et al. |
| 2002/0042372 | A1 | 4/2002 | Olsen et al. |

FOREIGN PATENT DOCUMENTS

| | | |
|---|---|---|
| WO | 93/23075 | 11/1993 |
| WO | 97/30065 | 8/1997 |
| WO | 98/31709 | 7/1998 |
| WO | 00/52051 | 9/2000 |
| WO | 00/55174 | 9/2000 |
| WO | WO 01/30969 | 5/2001 |
| WO | WO 01/32926 | 5/2001 |
| WO | 01/73025 | 10/2001 |

OTHER PUBLICATIONS

Office Action mailed Nov. 24, 2004 in U.S. Appl. No. 09/703,350.
Adams, R.H., et al., "Roles of ephrinB ligands and EphB receptors in cardiovascular development: demarcation of arterial/venous domains, vascular morphogenesis, and sprouting angiogenesis" *Genes and Development* 13(3):295-306 (1999).
Airenne, T., GenBank Accession No. U31201, record created Apr. 27, 1996.
Alberts et al. *Molecular Biology of the Cell, 3RD edition*, New York:Garland Publishing, Inc. pp. 465 (1994).
Amieva, M.R. et al., "Subcellular Localization of Moesin in Dynamic Filopodia, Retraction Fibers, and Other Structures Involved in Substrate Exploration, Attachment, and Cell-Cell Contacts" *Exp. Cell Res.* 219(1):180-196 (1995).
Antonarakis, S.E., GenBank Accession No. X91249, record created Aug. 21, 1996.
Arch, R.H. et al., "4-1BB and Ox40 Are Members of a Tumor Necrosis Factor (TNF)-Nerve Growth Factor Receptor Subfamily That Bind TNF Receptor-Associated Factors and Activate Nuclear Factor κB" *Mol Cell Biol* 18(1):558-565 (Jan. 1998).
Arnman, V. et al., "Interferon-γ modulates the fibrinolytic response in cultured human endothelial cells" *Thrombosis Research* 77(5):431-440 (1995).
Arpin, M. et al., "Functional differences between L- and T-plastin isoforms" *Journal of Cell Biology* 127(6 Pt 2):1995-2008 (1994).
Avanzi, G., et al., "GAS6 Inhibits Granulocyte Adhesion to Endothelial Cells" *Blood* 91(7):2334-40 (1998).
Baum et al., "Identification of OX40 ligand and Preliminary Characterization of its Activities on OX40 Receptor" *Circ. Shock* 44(1) : 30-34. (1994).
Baum, P.R., et al., GenBank Accession No. S76792, record created Jun. 2, 2000.
Bement et al., "Cloning and mRNA Expression of Human Unconventional Myosin-IC. A Homologue of Amoeboid Myosins-I with a Single IQ Motif and an SH3 domain" *J. Mol. Biol.* 243(2) :356-363 (1994).
Bement, W.M., GenBank Accession No. U14391, record created Mar. 7, 1995.
Berquin, I.M. and B.F. Sloane, "Cathepsin B expression in human tumors" *Adv. Exp. Med. Biol.*389 :281-94 (1996).
Bird, I.N., et al., "Homophilic PECAM-1 (CD31) interactions prevent endothelial cell apoptosis but do not support cell spreading or migration" *J. Cell Sci.* 112(12) :1989-1997 (1999).
Bussolino et al., "Hepatocyte Growth Factor is a Potent Angiogenic Factor Which Stimulates Endothelial Cell Motility and Growth" *Journal of Cell Biology* 119(3) :629-641 (Nov. 1992).
Cao, L. et al., "Human gastric adenocarcinoma cathepsin B: isolation and sequencing of full-length cDNAs and polymorphisms of the gene" *Gene* 139(2) :163-169. (1994).
Cao, L., et al., GenBank Accession No. L16510, record created Apr. 7, 1994.
Chan, S.J., et al., "Nucleotide and predicted amino acid sequences of cloned human and mouse preprocathepsin B cDNAs" *Proc. Natl. Acad. Sci. USA.* 83(20) :7721-7725. (1986).
Chan, S.J., et al., GenBank Accession No. M14221, record created Nov. 1, 1994.
Chang, A.C-M., et al., "A novel human cDNA highly homologous to the fish hormone stanniocalcin" *Mol. Cell. Endocrinol.* 112(2) :241-247. (1995).

(Continued)

*Primary Examiner*—Ruixiang Li
(74) *Attorney, Agent, or Firm*—Carol A. Fang; Genentech, Inc.

(57) ABSTRACT

The invention provides methods and compositions for modulating vascularization and angiogenesis, including selective modulation of stages of multi-step vascularization and angiogenesis.

9 Claims, 6 Drawing Sheets

OTHER PUBLICATIONS

Chang, A.C.-M., GenBank Accession No. U25997, record created Apr. 2, 1998.

Chen, H., et al., "Cloning of the cDNA for a Human Homologue of the *Drosophila* White Gene and Mapping to Chromosome 21q22.3" *Am. J. Hum. Genet.* 59(1) :66-75. (1996).

Coluccio, L.M., "Differential calmodulin binding to three myosin-1 isoforms from liver" *J. Cell. Sci.* 107(Pt 8) :2279-2284 (1994).

Couffinhal et al., "Animal Model: Mouse Model of Angiogenesis" *American Journal of Pathology* 152(6) :1667-1679 (1998).

Danilenko, D.M. et al., "Recombinant Rat Fibroblast Growth Factor-16: Structure and Biological Activity" *Archives of Biochemistry & Biophysics* 361(1) :34-46 (1999).

Davis and Camarillo, "An $\alpha 2\beta 1$ integrin-dependent pinocytic mechanism involving intracellular vacuole formation and coalescence regulates capillary lumen and tube formation in three-dimensional collagen matrix" *Experimental Cell Research* 224(1) :39-51 (Apr. 10, 1996).

Dick et al., "Cytoplasmic Dynein (ddlcl) Mutations Cause Morphogenetic Defects and Apoptotic Cell Death in *Drosophila melanogaster*" *Molecular & Cellular Biology* 16(5) :1966-1977 (May 1996).

Dick, T., et al., GenBank Accession No. U32944, record created Jul. 23, 1996.

Dickinson, J.L. et al., "The C-D interhelical domain of the serpin plasminogen activator inhibitor-type 2 is required for protection from TNF-$\alpha$ induced apoptosis" *Cell Death Differ* 5(2) :163-71 (1998).

Dillman, "Monoclonal Antibodies for Treating Cancer" *Annals of Internal Medicine* 111:592-603 (1989).

Docherty, A.J.P., GenBank Accession No. X05231, record created Mar. 30, 1995.

Dreesen, T.D. et al., "The Brown Protein of *Drosophila melanogaster* Is Similar to the White Protein and to Components of Active Transport Complexes" *Molecular & Cellular Biology* 8(12) :5206-15 (Dec. 1988).

Ferrara, N., "Role of Vascular Endothelial Growth Factor in Physiologic and Pathologic Angiogenesis: Therapeutic Implications" *Seminars in Oncology* 29(6) :Suppl. 16:10-14 (2002).

Filvaroff et al., "Stanniocalcin 1 Alters Muscle and Bone Structure and Function in Transgenic Mice" *Endocrinology* 143(9) :3681-3690 (2002).

Folkman et al., "Induction of angiogenesis during the transition from hyperplasia to neoplasia" *Nature* 339(6219) :58-61 (1989).

Folkman, J., "Role of Angiogenesis in Tumor Growth and Metastasis" *Seminars in Oncology* 29(6) :Suppl.16:15-18 (2002).

Freund, Y.R. and Blair, P.B., "Depression of Natural Killer Activity and Mitogen Responsiveness in Mice Treated with Pristane" *J. Immunol.* 129:2826-2830 (1982).

Fujiwara et al., "Assessment of Stanniocalcin-1 mRNA as a molecular marker for micrometastases of various human cancers" *Int. J. Oncol.* 16:799-804 (2000).

GenBank Accession No. NM_004431, record created Apr. 7, 2003.
GenBank Accession No. NM_005099, record created Apr. 6, 2003.
GenBank Accession No. P30530, record created Jun. 15, 2002.
GenBank Accession No. X03212, record created May 26, 1999.

Gerritsen et al., "In silico data filtering to identify new angiogenesis targets from a large in vitro gene profiling data set" *Physiol. Genomics* 10(1) :13-20 (2002).

Gerritsen et al., "Stanniocalcin: No Longer Just a Fish Tale" *Vitamins and Hormones* 70:105-135 (2005).

Glass et al., "Sequence and Expression of a Human Type II Mesothelial Keratin" *Journal of Cell Biology* 101(6) :2366-2373 (Dec. 1985).

Godfrey, W. et al., "Identification of a human OX-40 ligand, a costimulator of CD4+ T cells with homology to tumor necrosis factor" *J. Experimental Medicine* 180(2) :757-762 (Aug. 1994).

Hager, G. et al., "A peptide derived from a neurite outgrowth-promoting domain on the $\gamma$ 1 chain of laminin modulates the electrical properties of neocortical neurons" *Neuroscience* 86(4) :1145-54 (1998).

Hammond, C. et al., "The Tetraspan Protein CD82 Is a Resident of MHC Class II Compartments Where It Associates with HLA-DR, -DM, and -DO Molecules" *J. Immunol.* 161(7) :3282-91 (1998).

Hayashi et al., "Potential Role of Hepatocyte Growth Factor, a Novel Angiogenic GRowth Factor, in Peripheral Arterial Disease" *Circulation* 100(19 Suppl) :II-301-II-308 (1999).

Heath, P., GenBank Accession No. CAB87617 Record created: (Apr. 13, 2000).

Hennessy, et al., "Complete Thrombospondin mRNA Sequence Includes Potential Regulatory Sites in the 3' Untranslated Region" *Journal of Cell Biology* 108(2) :729-736 (Feb. 1989).

Hennessy, S.W., et al., GenBank Accession No. X14787, record created Mar. 31, 1995.

Hibi et al., "Molecular Cloning and Expression of an IL-6 Signal Transducer, gp130" *Cell* 63(6) :1149-1157 (Dec. 1990).

Hibi, M., et al., GenBank Accession No. M57230, record created Jan. 6, 1995.

Hibino et al., "Suppression of Keratinocyte Proliferation by Plasminogen Activator Inhibitor-2" *J Invest Dermatol* 112(1) :85-90 (1999).

Hirano, T., GenBank Accession No. D28137, record created Feb. 8, 2003.

Hisano et al., "Increased expression of T-plastin gene in cisplatin-resistant human cancer cells: identification by mRNA differential display" *FEBS Lett* 397(1) :101-7 (1996).

Hongo et al., "Development and Characterization of Murine Monoclonal Antibodies to the Latency-Associated Peptide of Transforming Growth Factor $\beta_1$," *Hybridoma* 14:253-260 (1995).

Iino et al., "Quantification and Characterization of Human Endothelial Cell-Derived Tissue Factor Pathway Inhibitor-2" *Arterioscler Thromb Vasc Biol* 18(1) :40-6 (1998).

Imura et al., "The Human OX40/gp34 System Directly Mediates Adhesion of Activated T Cells to Vascular Endothelial Cells" *Journal of Experimental Medicine* 183(5) :2185-2195 (May 1996).

Ishikawa et al., "Molecular Cloning and Chromosomal Mapping of a Bone Marrow Stromal Cell Surface Gene, BST2, That May Be Involved in Pre-B-Cell Growth" *Genomics* 26(3) :527-534 (1995).

Ishikawa et al., "Prediction of the Coding Sequences of Unidentified Human Genes. X. The Complete Sequences of 100 New cDNA Clones from Brain Which Can Code for Large Proteins in vitro" *DNA Res.* 5(3) :169-176 (1998).

Ito et al., "Angiogenesis but not collateral growth associated with ischemia after femoral artery occlusion" *Am. J. Physiol.* 273 (3 Pt 2) : H1255-H1265 (1997).

Itoh, N., GenBank Accession No. AB009391, record created Feb. 25, 1998.

Jain, R., "Barriers to drug delivery in solid tumors" *Scientific American* 271(1) :58-65 (Jul. 1994).

Janssen et al., "A novel putative tyrosine kinase receptor with oncogenic potential" *Oncogene* 6:2113-2120 (1991).

Jennische et al., "Expression of hepatocyte growth factor in growing and regenerating rat skeletal muscle" *Am J Physiol* 265(1 Pt 1) : C122-C128 (1993).

Kahn et al., "Gene Expression Profiling in an in Vitro Model of Angiogenesis" *American Journal of Pathology* 156(6) :1887-1900 (Jun. 2000).

Kallunki et al., "A Truncated Laminin Chain Homologous to the B2 Chain: Structure, Spatial Expression, and Chromosomal Assignment" *Journal of Cell Biology* 119(3) :679-693 (Nov. 1992).

Keppler et al., "Tumor progression and angiogenesis: cathepsin B & Co" *Biochem Cell Biol* 74(6) :799-810 (1996).

Kerlavage, A.R., GenBank Accession No. AA301555, record created Apr. 18, 1997.

Kerlavage, A.R., GenBank Accession No. AA332019, record created Apr. 21, 1997.

Kerlavage, A.R., GenBank Accession No. AA337670, record created Apr. 21, 1997.

Kerlavage, A.R., GenBank Accession No. AA363712, record created Apr. 21, 1997.

Kerlavage, A.R., GenBank Accession No. AA370299, record created Apr. 21, 1997.

Kershaw et al., "Molecular Cloning and Characterization of Human Podocalyxin-like Protein: orthologous relationship to rabbit PCLP1 and rat podocalyxin" *Journal of Biological Chemistry* 272(25) : 15708-15714 (1997).

Kershaw, D.B., et al., GenBank Accession No. U97519, record created Jun. 25, 1997.

Khaliq et al., "Increased Expression of Placenta Growth Factor in Proliferative Diabetic Retinopathy" *Laboratory Investigation* 78(1) : 109-116 (Jan. 1998).

Khaliq et al., "Localisation of Placenta Growth Factor (PlGF) in Human Term Placenta" *Growth Factors* 13(3-4) :243-50 (1996).

Kohfeldt et al., "Nidogen-2: A New Basement Membrane Protein with Diverse Binding Properties" *J Mol Biol* 282(1) :99-109 (1998).

Kohler and Milstein, "Continuous Cultures of Fused Cells Secreting Antibody of Predefined Specificity" *Nature* 256(5517) :495-497 (Aug. 7, 1975).

Koide et al., "Preparation of a Monoclonal Antibody Specific for Human Stanniocalcin" *Biol. Pharm. Bull.* 21(12) :1352-1355 (1998).

Kutty et al., "Molecular Characterization and Developmental Expression of NORPEG, a Novel Gene Induced by Retinoic Acid" *Journal of Biological Chemistry* 276(4) :2831-2840 (2001).

Kutty, R.K., et al., GenBank Accession No. AF155135, record created Jan. 22, 2001.

Lankes, W.T, and Furthmayr, H., "Moesin: A member of the protein 4.1-talin-ezrin family of proteins" *Proc. Natl. Acad. Sci. USA* 88:8297-8301 (Oct. 1991).

Lankes, W.T., and Furthmayr, H., GenBank Accession No. M69066, record created Apr. 27, 1993.

Lewin, B., "Regulation of transcription" *Genes VI*, NY:Oxford University Press, Inc., Chapter 29, pp. 847-848 (1997).

Li, H., et al., GenBank Accession No. AF151793, record created Nov. 15, 1999.

Liew, C.C., GenBank Accession No. N56435, record created Feb. 20, 1996.

Lin et al., "Human Plastin Genes: Comparative gene structure, chromosome location, and differential expression in normal and neoplastic cells" *J Biol Chem* 268(4) :2781-92 (1993).

Lin, C.S., et al., GenBank Accession No. L05491, record created Jan. 14, 1995.

Lindberg et al., "cDNA cloning and characterization of eck, and epithelial cell receptor protein-tyrosine kinase in the eph/elk family of protein kinases" *Molecular & Cellular Biology* 10(12) :6316-6324 (1990).

Lindberg, R.A., and Hunter, T., GenBank Accession No. M59371, record created Nov. 21, 1994.

Maglione et al., "Isolation of a human placenta cDNA coding for a protein related to the vascular permeability factor" *Proc. Natl. Acad. Sci.* 88:9267-9271 (1991).

Maulik et al., "Role of the hepatocyte growth factor receptor, c-Met, in oncogenesis and potential for therapeutic inhibition" *Cytokine & Growth Factor Reviews* 13(1) :41-59 (Feb. 2002).

McCloskey et al., "GAS6 Mediates Adhesion of Cells Expressing the Receptor Tyrosine Kinase Axl" *J Biol Chem* 272(37) :23285-23291 (Sep. 1997).

McCudden et al., "Characterization of Mammalian Stanniocalcin Receptors" *Journal of Biological Chemistry* 277:45249-45258 (2002).

Missotten et al., "Alix, a novel mouse protein undergoing calcium-dependent interaction with the apoptosis-linked-gene 2 (ALG-2) protein" *Cell Death Differ* 6(2) :124-9 (1999).

Miyake et al., "Structure and expression of a novel member, FGF-16, of the fibroblast growth factor family" *Biochemical & Biophysical Research Communications* 243(1) :148-152 (Feb. 4, 1998).

Miyazawa et al., "Molecular cloning and sequence analysis of cDNA for human hepatocyte growth factor" *Biochem. & Biophys. Res. Comm.* 163(2) :967-973 (Sep. 15, 1989).

Mook, O.R. et al., "The role of gelatinases in colorectal cancer progression and metastasis" *Biochimica et Biophysica Acta* 1705:69-89 (2004).

Morishita et al., "Hepatocyte Growth Factor as Cardiovascular Hormone: Role of HGF in the Pathogenesis of Cardiovascular Disease" *Endocrine Journal* 49:273-284 (2002).

Mosialos et al., "Epstein-Barr Virus Infection Induces Expression in B Lymphocytes of a Novel Gene Encoding an Evolutionarily Conserved 55-Kilodalton Actin-Bundling Protein" *Journal of Virology* 68(11) :7320-7328 (Nov. 1994).

Mosialos, G., GenBank Accession No. U09873, record created Feb. 14, 1995.

Mukaida et al., "Genomic structure of the human monocyte-derived neutrophil chemotactic factor IL-8" *J. Immunol.* 143(4) :1366-1371 (Aug. 15, 1989).

Mukaida, N., et al., GenBank Accession No. M28130, record created Jan. 6, 1995.

Nagira et al., "Mouse Homologue of C33 Antigen (CD82), a Member of the Transmembrane 4 Superfamily: Complementary DNA, Genomic Structure, and Expression" *Cell Immunol* 157(1) :144-57 (1994).

Nakamura et al., "Molecular Cloning and Expression of Human Hepatocyte Growth Factor" *Nature* 342:440-443 (Nov. 23, 1989).

Newman et al., "PECAM-1 (CD31) Cloning and Relation to Adhesion Molecules of the Immunoglobulin Gene Superfamily" *Science* 247:1219-1222 (Mar. 1990).

Newman, P.J., et al., GenBank Accession No. M28526, record created Apr. 27, 1993.

Nicosia et al., "Modulation of Angiogenesis in Vitro by Laminin-Entactin Complex" *Dev Biol* 164(1) :197-206 (1994).

O'Donnel et al., "Expression of Receptor Tyrosine Kinase Axl and its Ligand Gas6 in Rheumatoid Arthritis: Evidence for a Novel Endothelial Cell Survival Pathway" *Am J Pathol* 154(4) :1171-80 (Apr. 1999).

Ohno et al., GenBank Accession No. D86425, record created Mar. 11, 1998.

Okajima et al., "Primary Structure of Rat Hepatocyte Growth Factor and Induction of Its mRNA During Liver Regeneration Following Hepatic Injury" *European Journal of Biochemistry* 193(2) :375-381 (Oct. 24, 1990).

Olsen et al., "Human stanniocalcin: A possible hormonal regulator of mineral metabolism" *Proc. Natl. Acad. Sci. USA* 93(5) :1792-6 (1996).

Paciga et al., "Ovarian Stanniocalcin Is Structurally Unique in Mammals and Its Production and Release Are Regulated through the Luteinizing Hormone Receptor" *Endocrinology* 143:3925-3934 (2002).

Park et al., "Placenta growth factor. Potentiation of vascular endothelial growth factor bioactivity, in vitro and in vivo, and high affinity binding to Flt-1 but not to Flk-1/KDR" *Journal of Biological Chemistry* 269(41) :25646-54 (Oct. 14, 1994).

Persico, M.G., GenBank Accession No. X54936, record created Nov. 12, 1991.

Ponce et al., "Identification of Endothelial Cell Binding Sites on the Laminin γ1 Chain" *Circ Res* 84(6) :688-94 (1999).

Presta et al., "Humanization of an Anti-Vascular Endothelial Growth Factor Monoclonal Antibody for the Therapy of Solid Tumors and Other Disorders" *Cancer Research* 57(20) :4593-4599 (Oct. 15, 1997).

Rao et al., "Regulation of ProMMP-1 and ProMMP-3 Activation by Tissue Factor Pathway Inhibitor-2/Matrix-Associated Serine Protease Inhibitor" *Biochem Biophys Res Commun* 255(1) :94-98 (1999).

Sadoul, R., GenBank Accession No. AJ005073, record created Mar. 24, 1999.

Samia et al., "Chromosomal Organization and Localization of the Human Urokinase Inhibitor Gene: Perfect Structural Conservation with Ovalbumin" *Genomics* 6:159-167 (1990).

Samia, J.A., et al., GenBank Accession No. M31551, record created Aug. 3, 1993.

Samso et al., "Structural Characterization of a Dynein Motor Domain" *J Mol Biol* 276(5) :927-937 (1998).

Sassetti et al., "Identification of Podocalyxin-like Protein as a High Endothelial Venule Ligand for L-selectin: Parallels to CD34" *J Exp Med* 187(12) :1965-75 (Jun. 15, 1998).

Sawano et al., "Flt-1 but not KDR/Flk-1 tyrosine kinase is a receptor for placenta growth factor, which is related to vascular endothelial growth factor" *Cell Growth & Differentiation* 7(2) :213-221 (Feb. 1996).

Schmidt et al., "Levels of Vascular Endothelial Growth Factor, Hepatocyte Growth Factor/Scatter Factor and Basic Fibroblast Growth Factor in Human Gliomas and Their Relation to Angiogenesis" *Int. J. Cancer* 84(1):10-18 (1999).

Scholz et al., "Ultrastructure and molecular histology of rabbit hindlimb collateral artery growth (artereiogenesis)" *Virchows Arch* 436(3):257-70 (2000).

Schulz, A., GenBank Accession No. X57019, record created Aug. 7, 2001.

Seki et al., "Isolation and Expression of cDNA for Different Forms of Hepatocyte Growth Factor from Human Leukocyte" *Biochem. and Biophys. Res. Commun.* 172(1):321-327 (Oct. 15, 1990).

Shimkets et al., "Gene expression analysis by transcript profiling coupled to a gene database query" *Nature Biotechnology* 17(8):798-803 (Aug. 1999).

Shinoda et al., "Tissue Factor Pathway Inhibitor-2 Is a Novel Mitogen for Vascular Smooth Muscle Cells" *J Biol Chem* 274(9):5379-84 (1999).

Sprecher et al., "Molecular cloning, expression, and partial characterization of a second human tissue-factor-pathway inhibitor" *Proc. Natl. Acad. Sci.* USA 91(8):3353-3357 (Apr. 1994).

Sprecher, C.A., et al., GenBank Accession No. L27624, record created Jul. 27, 1994.

Strausberg, R., GenBank Accession No. AW076072, record created Oct. 13, 1999.

Sundstrom, B.E. and T.I. Stigbrand, "Cytokeratins and tissue polypeptide antigen" *Int J Biol Markers* 9(2):102-8 (1994).

Taga, T. and T. Kishimoto, "GP130 and the interleukin-6 family of cytokines" *Annu Rev Immunol* 15:797-819 (1997).

Takada, Y. and Hemler, M.E., "The Primary Structure of the VLA-2/Collagen Receptor α2 Subunit (Platelet GPIa): Homology to Other Integrins and the Presence of a Possible Collagen-binding Domain" *Journal of Cell Biology* 109(1):397-407 (Jul. 1989).

Takada, Y. and Henler, M.E., GenBank Accession No. X17033, record created Mar. 5, 1999.

Tashiro et al., "Deduced Primary Structure of Rat Hepatocyte Growth Factor and Expression of the mRNA in Rat Tissues" *Proc. Natl. Acad. Sci.* USA 87(8):3200-3204 (Apr. 1990).

To et al., "The roles of hepatocyte growth factor/scatter factor and Met receptor in human cancers (Review)" *Oncol Rep* 5(5):1013-1024 (1998).

Tortorella et al., "Purification and Cloning of Aggrecanase-1: A Member of the ADAMTS Family of Proteins" *Science* 284:1664-1666 (1999).

Varghese et al., "Overexpression of Human Stanniocalcin Affects Growth and Reproduction in Transgenic Mice" *Endocrinology* 143:868-876 (2002).

Vazquez et al., "METH-1, and Human Otholog of ADAMTS-1, and METH-2 Are Members of a New Family of Proteins with Angioinhibitory Activity" *J Biol Chem* 274(33):23349-57 (1999).

Wagner et al., "Human Stanniocalcin Inhibits Renal Phosphate Excretion in the Rat" *Journal of Bone and Mineral Research* 12(2):165-171 (1997).

Wagner et al., "Immunological and biological evidence for a stanniocalcin-like hormone in human kidney" *Proc. Natl. Acad. Sci.* USA 92(6):1871-5 (1995).

Wagner et al., "Molecular cloning and cDNA sequence analysis of coho salmon stanniocalcin" *Molecular and Cellular Endocrinology* 90(1):7-15 (1992).

Wagner et al., "Purification, Characterization, and Bioassay of Teleocalcin, a Glycoprotein from Salmon Corpuscles of Stannius" *General and Comparative Endocrinology* 63:481-491 (1986).

Wary et al., "Analysis of VEGF-responsive Genes Involved in the activation of endothelial cells" *Molecular Cancer* 2(25) (Jul. 9, 2003).

Waterston, R., GenBank Accession No. AC002076, record created Jun. 4, 2002.

Weidner et al., "Tumor angiogenesis and metastasis—correlation in invasive breast carcinoma" *New England J. of Medicine* 324(1):1-8 (1991).

Weiner, L.M., "An overview of monoclonal antibody therapy of cancer" *Seminars in Oncology* 26(4):41-50 (Aug. 1999).

Whitham S.E. et al., "Comparison of human stromelysin and collagenase by cloning and sequence analysis" *Biochemical Journal* 240(3):913-916 (1986).

Wilson, R.K., "WashU-Merck EST Project" GenBank Accession No. W38656, record created May 15, 1996.

Wilson, R.K., "WashU-Merck EST Project" GenBank Accession No. W77963, record created Oct. 17, 1996.

Wilson, R.K., "WashU-NCI human EST Project" GenBank Accession No. AA984515, record created May 27, 1998.

Wilson, R.K., GenBank Accession No. AA088472, record created Oct. 24, 1996.

Wilson, R.K., GenBank Accession No. AA196914, record created Jan. 22, 1997.

Wilson, R.K., GenBank Accession No. N73108, record created Jan. 28, 1997.

Wilson, R.K., GenBank Accession No. T53906, record created Feb. 6, 1995.

Xin et al., "Hepatocyte Growth Factor Enhances Vascular Endothelial Growth Factor-Induced Angiogenesis in Vitro an in Vivo" *Am. J. Pathol.* 158(3):1111-1120 (2001).

Yamashiro et al., "Fascin, an Actin-bundling Protein, Induces Membrane Protrusions and Increases Cell Motility of Epithelial Cells" *Mol Biol Cell* 9(5):993-1006 (May 1998).

Zhao et al., "Purification and Cloning of PZR, a Binding Protein and Putative Physiological Substrate of Tyrosine Phosphatase SHP-2" *Journal of Biological Chemistry* 273(45):29367-29372 (Nov. 6, 1998).

Zhao, Z.J., and Zhao, R., GenBank Accession No. AF087020, record created Nov. 8, 1998.

Zhou, R., "The Eph Family Receptors and Ligands" *Pharmacol Ther* 77(3):151-81 (1998).

Ziche et al., "Placenta Growth Factor-1 is Chemotactic, Mitogenic, and Angiogenic" *Lab Invest* 76(4):517-531 (Apr. 1997).

Zlot et al., "Stanniocalcin 1 Is an Autocrine Modulator of Endothelial Angiogenic Responses to Hepatocyte Growth Factor" *The Journal of Biological Chemistry* 278(48):47654-47659 (2003).

Zoellner et al., "Cytokine Regulation of the Synthesis of Plasminogen Activator Inhibitor-2 by Human Vascular Endothelial Cells. Comparison with Plasminogen Activator Inhibitor-1 Synthesis" *Thromb Haemost* 69(2):135-140 (1993).

FIG. 3A  FIG. 3B

```
CAGTTTGCAAAAGCCAGAGGTGCAAGAAGCAGCGACTGCAGCAGCAGCAGCAGCGGC
GGTGGCAGCAGCAGCAGCAGCGGCGGCAGCAGCAGCAGCAGCGGAGGCACCGGTGGCAGC
AGCAGCATCACCAGCAACAACAACAAAAAAAAATCCTCATCAAATCCTCACCTAAGCTTT
CAGTGTATCCAGATCCACATCTTCACTCAAGCCAGGAGAGGGAAAGAGGAAAGGGGGGCA
GGAAAAAAAAAAAACCCAACAACTTAGCGGAAACTTCTCAGAGAATGCTCCAAAACTCAG
CAGTGCTTCTGGTGCTGGTGATCAGTGCTTCTGCAACCCATGAGGCGGAGCAGAATGACT
CTGTGAGCCCCAGGAAATCCCGAGTGGCGGCTCAAAACTCAGCTGAAGTGGTTCGTTGCC
TCAACAGTGCTCTACAGGTCGGCTGCGGGGCTTTTGCATGCCTGGAAAACTCCACCTGTG
ACACAGATGGGATGTATGACATCTGTAAATCCTTCTTGTACAGCGCTGCTAAATTTGACA
CTCAGGGAAAGCATTCGTCAAAGAGAGCTTAAAATGCATCGCCAACGGGGTCACCTCCA
AGGTCTTCCTCGCCATTCGGAGGTGCTCCACTTTCCAAAGGATGATTGCTGAGGTGCAGG
AAGAGTGCTACAGCAAGCTGAATGTGTGCAGCATCGCCAAGCGGAACCCTGAAGCCATCA
CTGAGGTCGTCCAGCTGCCCAATCACTTCTCCAACAGATACTATAACAGACTTGTCCGAA
GCCTGCTGGAATGTGATGAAGACACAGTCAGCACAATCAGAGACAGCCTGATGGAGAAAA
TTGGGCCTAACATGGCCAGCCTCTTCCACATCCTGCAGACAGACCACTGTGCCCAAACAC
ACCCACGAGCTGACTTCAACAGGAGACGCACCAATGAGCCGCAGAAGCTGAAAGTCCTCC
TCAGGAACCTCCGAGGTGAGGAGGACTCTCCCTCCCACATCAAACGCACATCCCATGAGA
GTGCATAACCAGGGAGAGGTTATTCACAACCTCACCAAACTAGTATCATTTTAGGGGTGT
TGACACACCAATTTTGAGTGTACTGTGCCTGGTTTGATTTTTTTAAAGTAGTTCCTATTT
TCTATCCCCCTTAAAGAAAATTGCATGAAACTAGGCTTCTGTAATCAATATCCCAACATT
CTGCAATGGCAGCATTCCCACCAACAAAATCCATGTGATCATTCTGCCTCTCCTCAGGAG
AAAGTACCCTCTTTTACCAACTTCCTCTGCCATGTCTTTTCCCCTGCTCCCCTGAGACCA
CCCCCAAACACAAAACATTCATGTAACTCTCCAGCCATTGTAATTTGAAGATGTGGATCC
CTTTAGAACGGTTGCCCCAGTAGAGTTAGCTGATAAGGAAACTTTATTTAAATGCATGTC
TTAAATGCTCATAAAGATGTTAAATGGAATTCGTGTTATGAATCTGTGCTGGCCATGGAC
GAATATGAATGTCACATTTGAATTCTTGATCTCTAATGAGCTAGTGTCTTATGGTCTTGA
TCCTCCAATGTCTAATTTTCTTTCCGACACATTTACCAAATTGCTTGAGCCTGGCTGTCC
AACCAGACTTTGAGCCTGCATCTTCTTGCATCTAATGAAAACAAAAAGCTAACATCTTT
ACGTACTGTAACTGCTCAGAGCTTTAAAAGTATCTTTAACAATTGTCTTAAAACCAGAGA
ATCTTAAGGTCTAACTGTGGAATATAAATAGCTGAAAACTAATGTACTGTACATAAATTC
CAGAGGACTCTGCTTAAACAAAGCAGTATATAATAACTTTATTGCATATAGATTTAGTTT
TGTAACTTAGCTTTATTTTTCTTTTCCTGGGAATGGAATAACTATCTCACTTCCAGATAT
CCACATAAATGCTCCTTGTGGCCTTTTTTATAACTAAGGGGTAGAAGTAGTTTTAATTC
AACATCAAAACTTAAGATGGGCCTGTATGAGACAGGAAAAACCAACAGGTTTATCTGAAG
GACCCCAGGTAAGATGTTAATCTCCCAGCCCACCTCAACCCAGAGGCTACTCTTGACTTA
GACCTATACTGAAAGATCTCTGTCACATCCAACTGGAAATTCCAGGAACCAAAAAGAGCA
TCCCTATGGGCTTGGACCACTTACAGTGTGATAAGGCCTACTATACATTAGGAAGTGGTA
GTTCTTTACTCGTCCCCTTTCATCGGTGCCTGGTACTCTGGCAAATGATGATGGGGTGGG
AGACTTTCCATTAAATCAATCAGGAATGAGTCAATCAGCCTTTAGGTCTTTAGTCCGGGG
GACTTGGGGCTGAGAGAGTATAAATAACCCTGGGCTGTCCAGCCTTAATAGACTTCTCTT
ACATTTCGTCCTGTAGCACGCTGCCTGCCAAAGTAGTCCTGGCAGCTGGACCATCTCTG
TAGGATCGTAAAAAATAGAAAAAAGAAAAAAAAAGAAAGAAAGAGGGAAAAGAGCT
GGTGGTTTGATCATTTCTGCCATGATGTTTACAAGATGGCGACCACCAAAGTCAAACGAC
TAACCTATCTATGAACAACAGTAGTTTCTCAGGGTCACTGTCCTTGAACCCAACAGTCCC
```

*FIG. 6A*

```
TTATGAGCGTCACTGCCCACCAAAGGTCAATGTCAAGAGAGGAAGAGAGGGAGGAGGGGT
AGGACTGCAGGGGCCACTCCAAACTCGCTTAGGTAGAAACTATTGGTGCTCGACTCTCAC
TAGGCTAAACTCAAGATTTGACCAAATCGAGTGATAGGGATCCTGGTGGGAGGAGAGAGG
GCACATCTCCAGAAAAATGAAAAGCAATACAACTTTACCATAAAGCCTTTAAAACCAGTA
ACGTGCTGCTCAAGGACCAAGAGCAATTGCAGCAGACCCAGCAGCAGCAGCAGCAGCACA
AACATTGCTGCCTTTGTCCCCACACAGCCTCTAAGCGTGCTGACATCAGATTGTTAAGGG
CATTTTTATACTCAGAACTGTCCCATCCCCAGGTCCCCAAACTTATGGACACTGCCTTAG
CCTCTTGGAAATCAGGTAGACCATATTCTAAGTTAGACTCTTCCCCTCCCTCCCACACTT
CCCACCCCCAGGCAAGGCTGACTTCTCTGAATCAGAAAAGCTATTAAAGTTTGTGTGTTG
TGTCCATTTTGCAAACCCAACTAAGCCAGGACCCCAATGCGACAAGTAGTTCATGAGTAT
TCCTAGCAAATTTCTCTCTTTCTTCAGTTCAGTAGATTTCCTTTTTTCTTTTCTTTTTTT
TTTTTTTTTTTTTTGGCTGTGACCTCTTCAAACCGTGGTACCCCCCTTTTCTCCCCAC
GATGATATCTATATATGTATCTACAATACATATATCTACACATACAGAAAGAAGCAGTTC
TCACATGTTGCTAGTTTTTGCTTCTCTTTCCCCCACCCTACTCCCTCCAATTCCCCCCT
TAAACTTCCAAAGCTTCGTCTTGTGTTTGCTGCAGAGTGATTCGGGGCTGACCTAGACC
AGTTTGCATGATTCTTCTCTTGTGATTTGGTTGCACTTTAGACATTTTGTGCCATTATA
TTTGCATTATGTATTTATAATTTAAATGATATTTAGGTTTTGGCTGAGTACTGGAATAA
ACAGTGAGCATATCTGGTATATGTCATTATTTATTGTTAAATTACATTTTTTAAGCTCCA
TGTGCATATAAAGGTTATGAAACATATCATGGTAATGACAGATGCAAGTTATTTATTTG
CTTATTTTTTATAATTAAAGATGCCATAGCATAATATGAAGCCTTTGGTGAATTCCTTCT
AAGATAAAAATAATAATAAAGTGTTACGTTTTATTGGTTTCAAAAAAAAAAAAAAAAAA
A (SEQ ID NO:1)

MLQNSAVLLVLVISASATHEAEQNDSVSPRKSRVAAQNSAEVVRCLNSALQVGCGAFACL
ENSTCDTDGMYDICKSFLYSAAKFDTQGKAFVKESLKCIANGVTSKVFLAIRRCSTFQRM
IAEVQEECYSKLNVCSIAKRNPEAITEVVQLPNHFSNRYYNRLVRSLLECDEDTVSTIRD
SLMEKIGPNMASLFHILQTDHCAQTHPRADFNRRRTNEPQKLKVLLRNLRGEEDSPSHIK
RTSHESA (SEQ ID NO:2)
```

*FIG. 6B*

METHODS AND COMPOSITIONS FOR SELECTIVE MODULATION OF VASCULARIZATION

RELATED APPLICATIONS

This application is a continuation of U.S. Ser. No. 10,824,075 filed Apr. 14, 2004, now U.S. Pat. No. 7,407,660, which is a non-provisional application filed under 37 C.F.R. 1.53(b)(1), claiming priority under 35USC 119(e) to provisional application No. 60/463,226 filed Apr. 16, 2003m, the contents of which are incorporated herein in their entirety by reference.

TECHNICAL FIELD

The present invention relates generally to the fields of molecular biology and vascularization. More specifically, the invention concerns modulators of angiogenesis, and uses thereof.

BACKGROUND

Stanniocalcin 1 (STC-1) is a secreted glycoprotein originally described as a hormone involved in the calcium and phosphate homeostasis in bony fishes. The mammalian homolog of this molecule has been identified as being highly upregulated in an in vitro model of angiogenesis as well as highly expressed at sites of pathological angiogenesis (e.g. tumor vasculature). See, for e.g., Kahn et al., Am. J. Pathol. (2000), 156(6):1887-1900. Its potential role in pathological conditions such as cancer has also been suggested. See, for e.g., Fujiwara et al., Int. J. Oncol. (2000), 16:799-804. Preparation of an antibody for a human STC-1 peptide is reported in Koide et al., Biol. Pharm. Bull. (1998), 21(12):1352-1355. However, the precise role of STC-1 in the angiogenesis process is unclear.

Numerous factors that promote or inhibit angiogenesis have been identified, reflecting the importance of the role of angiogenesis in homeostasis and pathological conditions. See, for e.g., Folkman, Seminars in Oncol. (2002), 29(6)(Suppl. 16):15-18; Ferrara, Seminars in Oncol. (2002), 29(6)(Suppl. 16): 10-14. Well-known angiogenic promoters include vascular endothelial growth factor (VEGF) and hepatocyte growth factor (HGF).

HGF is a mesenchyme-derived pleiotrophic factor with mitogenic, motogenic and morphogenic activities on a number of different cell types. HGF effects are mediated through a specific tyrosine kinase, c-met, and aberrant HGF and c-met expression are frequently observed in a variety of tumors. See, for e.g., Maulik et al., Cytokine & Growth Factor Reviews (2002), 13:41-59. Recent studies have shown HGF to be a potent growth factor implicated in wound healing, tissue regeneration and angiogenesis.

It was also recently reported that HGF, and more potently, HGF in combination with VEGF, synergistically induced vascular morphogenesis in vitro and angiogenesis in vivo (1). The gene expression profile of endothelial cells undergoing HGF and VEGF stimulated morphogenesis using Affmetrix™ oligonucleotide arrays was also analyzed. The homodimeric secreted glycoprotein, Stanniocalcin-1 (STC-1), was shown as one of the most highly upregulated genes in this in vitro model (2). Intense expression of STC-1 was observed in the vasculature of colon carcinomas (2). However, the precise nature of the role(s) of STC-1 in vascularization generally, and angiogenesis specifically, remains heretofore unclear.

All references cited herein, including patent applications and publications, are incorporated by reference in their entirety.

DISCLOSURE OF THE INVENTION

Methods of the invention are based generally on the finding that certain angiogenic modulators selectively affect some stages of the angiogenic process but not others. It is also herein disclosed that certain angiogenic modulators are capable of affecting angiogenesis induced by some angiogenic promoters but not others. Thus, these factors provide unique and advantageous targets for greater fine-tuning in designing prophylactic and/or therapeutic approaches against pathological conditions associated with abnormal angiogenic states. Accordingly, the invention provides methods, compositions, kits and articles of manufacture for modulation of angiogenesis. The invention is particularly useful for modulation of specific stages in the multi-stage process of angiogenesis. In particular, modulators and methods of the invention are based on regulating certain stages of the angiogenesis process in disease states wherein abnormal angiogenesis occurs. The invention is also especially useful for modulation of extent or amount of angiogenesis, for example by inhibiting the angiogenic process, or subset stages thereof, promoted by one angiogenic promoter but not the angiogenesis process promoted by another angiogenic promoter. Since angiogenesis is important in homeostasis and normal physiological functions, the ability to reduce but not eliminate (or substantially inhibit) angiogenesis would provide a great advantage in therapeutic designs wherein it may be desirable to reduce but not eliminate angiogenesis in a single tissue and/or subject. Hence, compositions and methods of the invention provide unique advantages in overcoming difficulties inherent in the complexities of the angiogenic process and the related difficulties of therapeutically addressing disease states associated with pathological angiogenic states.

In one aspect, the invention provides methods of modulating angiogenesis comprising administering to a cell undergoing the angiogenic process an effective amount of stanniocalcin-1 (STC-1) or variant (as further defined below) thereof. The cell undergoing the angiogenic process may be present in an in vitro culture, an ex vivo culture or in vivo. In one embodiment, the cell is an endothelial cell.

In one embodiment, migration or morphogenesis of the cell undergoing the angiogenic process (which is generally an endothelial cell) is substantially inhibited.

In one embodiment, the vascularization or angiogenic process of methods of the invention is associated with presence of hepatocyte growth factor (HGF). Said HGF may be expressed in the cell undergoing the angiogenic process, a neighboring cell and/or which is present systemically. Said HGF may also be provided exogenously. In some embodiments, expression or presence of hepatocyte growth factor occurs prior to and/or parallels initiation of the angiogenic process.

In some embodiments, modulation by STC-1 or variant thereof in methods of the invention is substantially inhibited by an antagonist of STC-1. In some embodiments, said antagonist is an antibody or fragment thereof. Such antagonists can be generated using methods known in the art, including those described herein. The invention also provides monoclonal antibodies, including blocking antibodies useful in, for example, methods of the invention. Antibodies of the invention include antibodies produced by hybridoma clones designated 3E10.1F5.1D11 (ATCC Deposit No. PTA-5100), 21F4.2F11.1H12 (ATCC Deposit No. PTA-5103), 1F10.2F12.1E7 (ATCC Deposit No. PTA-5101), 18F1.1E6.1B10 (ATCC Deposit No. PTA-5099) and 12C3.2F3.2D8 (ATCC Deposit No. PTA-5102). The invention also provides antibodies that bind to substantially the same STC-1 epitope as antibodies produced by these hybridomas. In some embodiments, antibodies of the invention bind to or at the same STC-1 epitope as antibodies produced by these hybridomas. In some embodiments, antibodies of the invention compete with antibodies produced by these hybridomas in binding to STC-1. In one embodiment, an antibody of the invention is not an anti-peptide antibody. In one embodiment, an antibody of the invention does not bind to the sequence CYNRLVRSLLEADEDTVSTI (SEQ ID NO:3). In one embodiment, an antibody of the invention does not compete for binding to STC-1 with an antibody that binds to the sequence CYNRLVRSLLEADEDTVSTI (SEQ ID NO:3). Variable domain sequences, including CDR sequences, of the antibodies described herein can be easily determined using techniques known the art. Antibodies and immunoglobulin polypeptides comprising the heavy and/or light chain variable domain sequences of the antibodies described herein are also provided. In some embodiments, the invention provides antibodies and immunoglobulin polypeptides comprising the sequence of at least one, at least two, or all three CDRs of the heavy and/or light chain of the antibodies described herein. In one embodiment, an antibody of the invention is a monoclonal antibody, which in some embodiments is a chimeric/humanized or human antibody, or functional fragment thereof. These antibodies and immunoglobulin polypeptides would be useful in methods of the invention as long as they retain the STC-1 binding capability of the antibodies designated herein. Other antagonists are known in the art, including antisense oligonucleotides, small molecules and other inhibitory chemical compounds (such as organic and inorganic molecules). These antagonists can be produced by methods known in the art, including those disclosed herein.

Many angiogenic factors have been identified, and often cells undergoing angiogenesis are exposed to more than one angiogenic factor. Yet, the downstream effects of these factors in effecting angiogenesis are not fully elucidated. The present invention has identified a factor that selectively modulates some but not all stages of angiogenesis, in the angiogenic response of cells to some but not all angiogenic factors. Accordingly, in another aspect, the invention provides methods of selectively inhibiting angiogenesis promoted by a first angiogenic factor but not angiogenesis promoted by a second angiogenic factor, comprising administering to a cell exposed to both factors an effective amount of STC-1 or a variant thereof, wherein said STC-1 or variant thereof inhibits at least one step of the angiogenic process promoted by the first angiogenic factor but not the angiogenic process promoted by the second angiogenic factor In some embodiments of methods of the invention, the first and second angiogenic factors both are capable of inducing endogenous expression of STC-1. In one embodiment, the first angiogenic factor is hepatocyte growth factor. In another embodiment, the second angiogenic factor is basic fibroblast growth factor (bFGF). In some embodiments, the first angiogenic factor is hepatocyte growth factor and the second angiogenic factor is vascular endothelial growth factor (VEGF) and/or bFGF.

In some embodiments of methods of the invention, STC-1 or variant thereof inhibits or substantially inhibits cell migration and/or morphogenesis induced by or associated with exposure of the cell to the first angiogenic factor. In certain embodiments, STC-1 or variant thereof does not inhibit or substantially inhibit cell proliferation.

In some embodiments of methods of the invention, STC-1 or variant thereof does not inhibit or substantially inhibit cell migration and/or morphogenesis induced by or associated with exposure of the cell to the second angiogenic factor.

Generally, and preferably, the cell undergoing angiogenesis in any method of the invention is of endothelial origin.

In another aspect, the invention provides polypeptides comprising an amino acid sequence of at least 80%, 85%, 90%, 95%, 98%, 99% identity to the sequence of human STC-1 (as provided herein in FIG. 6), wherein an effective amount said polypeptide substantially inhibits at least one, but not all, of the stages of multi-stage angiogenic process. The angiogenic process is preferably induced by or associated with the presence of hepatocyte growth factor. Expression of polypeptides of the invention may be induced by any one or combination of factors, including factors in the group consisting of IL-1β, bFGF, HGF, IL-6 and IL-4.

In some embodiments, polypeptides of the invention inhibit or substantially inhibit endothelial cell migration and/or morphogenesis but do not inhibit or substantially inhibit endothelial cell proliferation.

In some embodiments, a polypeptide of the invention does not substantially reduce c-met phosphorylation, for example in an endothelial cell.

In another aspect, the invention provides polynucleotides encoding any of the polypeptides of the invention.

In another aspect, the invention provides antagonists, such as antibodies (or fragments thereof), against STC-1. Examples of these antibodies include those described herein. In some embodiments, these antibodies are capable of neutralizing or blocking STC-1 activity or function, examples of which include antibodies described herein. Other antagonists of STC-1 are also provided, such as small molecules, peptides, etc. These antagonists can be readily screened for by methods known in the art, including the assays and/or methods of screening, and biological readouts as described herein.

In another aspect, the invention provides methods of substantially inhibiting vascularization (for example, angiogenesis) in a mammal (for example, human), comprising administering to the mammal an effective amount of STC-1 or variant thereof. Said vascularization may be induced by or associated with presence of hepatocyte growth factor.

In another aspect, the invention provides methods of screening for a substance that selectively inhibits HGF-induced vascularization (for example, angiogenesis), said methods comprising comparing extent of inhibition when an endothelial cell is exposed to said substance with the extent of inhibition when the cell is exposed to STC-1 or an STC-1 agonist. Thus, in one aspect, the invention provides STC-1 agonists, such as a small molecule (including peptides, antibodies or fragments thereof, organic and inorganic molecules) that mimics and/or enhances the function/activity of STC-1 in inhibiting angiogenesis as described herein.

In another aspect, the invention provides methods of screening for a substance that selectively promotes HGF-induced vascularization (for example, angiogenesis), said methods comprising comparing the extent of vascularization (for example, angiogenesis) when an endothelial cell is exposed to said substance with the extent of vascularization (for example, angiogenesis) when the cell is exposed to an antagonist of STC-1 (for example, an antibody as described herein).

In another aspect, the invention provides methods of promoting vascularization (for example, angiogenesis) in a mammal (for example, human), comprising administering to the mammal an effective amount of an antagonist of STC-1 or variant thereof. Said vascularization may be induced by or associated with presence of hepatocyte growth factor.

In another aspect, the invention provides methods of diagnosis for conditions associated with activation of the HGF/c-met pathway or HGF-induced angiogenesis, comprising detecting presence and/or amount of STC-1 or STC-1 activity in a sample of interest. As appropriate, a reference sample (for e.g., that comprising a normal corresponding tissue) known or thought to exhibit a baseline amount of STC-1 or STC-1 activity may be used in these methods. These methods are particularly useful where it is desirable to detect and/or quantitate downstream effects/events of an axis known or suspected to be involved in a pathological condition associated with HGF/c-met induced angiogenesis. For example, presence and/or degree of these downstream effects (such as STC-1 activation/expression/activity) may serve as better or more accurate indicators of extent of the pathological condition. Thus, for example, degree of STC-1 induction/expression/activity may provide an indication of the role/extent of angiogenesis in an HGF/c-met induced pathological condition.

In methods of the invention, STC-1 may be provided as a polypeptide (including any described herein) or polynucleotide encoding said polypeptide. Examples of a polynucleotide encoding STC-1 include a polynucleotide comprising the nucleic acid sequence of SEQ ID NO:1 (FIG. 6), a polynucleotide encoding the amino acid sequence of SEQ ID NO:2 (FIG. 6) and a polynucleotide encoding an STC-1 variant (as described more extensively below).

BRIEF DESCRIPTION OF THE DRAWINGS

FIGS. 3A-C. STC-1 reduces endothelial cord formation on Matrigel induced by 20 ng/ml HGF. A. HGF+boiled STC-1 (250 ng/ml) B. HGF+native STC-1 (250 ng/ml) C. Quantitation of cord formation in the presence of boiled STC-1 (solid bars) or native STC-1 (hatched bars). Data shown are the mean ±SEM network area/well of three independent experiments. * significantly different from boiled control.

Figure 1A:
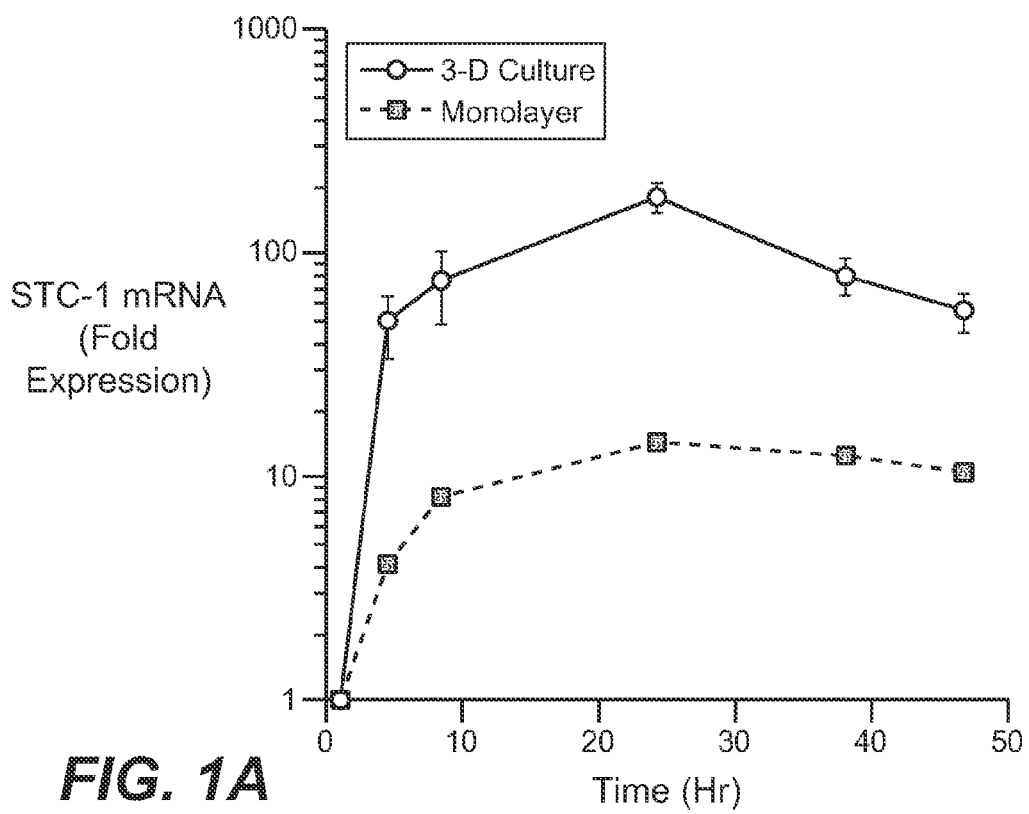
FIGS. 1A-B. STC-1 mRNA and protein are selectively upregulated in 3-D gel environments. A. STC-1 mRNA from HUVECs cultured in (3-D) or on the surface of (monolayer) collagen gels in BM supplemented with HGF (200 ng/mL) and VEGF (200 ng/mL). Duplicate samples were analyzed by quantitative RT-PCR (Taqman) as described in Example 1. Results are expressed as the ratio of STC-1 mRNA level to the level of Cyclophillin, a housekeeping gene, in the same sample. B. STC-1 protein from HUVECs cultured in (3-D) or on the surface of (monolayer) collagen gels in BM supplemented with HGF (200 ng/mL) and VEGF (200 ng/mL). STC-1 protein was determined by ELISA as described in Example 1. Values shown are the mean ±S.E.M., n=8. * significantly different from value at t=0, p<0.05

A. STC-1 and CD31 mRNA in gastrocnemius muscles removed from mice following sham surgery or femoral ligation. B. HGF mRNA in gastrocnemius muscles removed from mice following sham surgery or femoral ligation. Values are expressed as the mean ±S.E.M., n=6 mice per time point and treatment.

FIGS. 6A-B. STC-1 sequences. Nucleic acid (SEQ ID NO:1) and amino acid (SEQ ID NO:2) sequences of human STC-1.

MODES FOR CARRYING OUT THE INVENTION

The invention provides methods, compositions, kits and articles of manufacture for selective modulation of vascularization/angiogenesis.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Definitions

The term "STC-1 polypeptide", as used herein, refers to a polypeptide comprising the amino acid sequence listed in FIG. 6 (SEQ ID NO: 2) and STC-1 polypeptide variants (as further defined below). An STC-1 polypeptide may be isolated from a variety of sources, such as from human tissue types or from another source, or prepared by recombinant or synthetic methods.

"STC-1 polypeptide variants," as used herein, refers to a polypeptide having at least one of the biological activities of the STC-1 polypeptides as described herein (including at least an ability to inhibit at least one stage of the multi-stage HGF-induced angiogenic process) and having at least about 80% amino acid sequence identity with SEQ ID NO: 2 (as listed in FIG. 6). Ordinarily, an STC-1 polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to SEQ ID NO: 2 (FIG. 6). Ordinarily, STC-1 polypeptide variants are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the STC-1 polypeptide sequence (i.e., SEQ ID NO: 2) identified herein is defined as the percentage of amino acid residues in a candidate sequence that are identical with the amino acid residues in the specific STC-1 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 2 below. The ALIGN-2 sequence comparison computer program was authored by Genentech, Inc. and the source code shown in Table 2 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 2 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X", "Y". and "Z" each represent different hypothetical amino acid residues.

Unless specifically stated otherwise, all % amino acid sequence identity values used herein are obtained as described in the immediately preceding paragraph using the ALIGN-2 computer program.

Table 2

```
/*
 *
 * C-C increased from 12 to 15
 * Z is average of EQ
 * B is average of ND
 * match with stop is _M; stop-stop = 0; J (joker) match = 0
 */
define   _M      -8        /* value of a match with a stop */ int       _day[26][26] = {
```

```
        if (fj) {
                (void) unlink(jname);
                fj = 0;
                offset = 0;
        }                                       }

/*
 * write a filled jmp struct offset of the prev one (if any): nw()
 */
writejmps(ix)                                                                           writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
```

```
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0,-0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M,
         0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};

/*
*/
#include <stdio.h>
include <ctype.h> define  MAXJMP    16      /* max jumps in a diag */
define  MAXGAP    24      /* don't continue to penalize gaps larger than this */
#define  JMPS      1024    /* max jmps in an path */
define  MX        4       /* save if there's at least MX-1 bases since last jmp */ define  DMAT      3       /* value of matching bases */
define  DMIS      0       /* penalty for mismatched bases */
#define  DINS0     8       /* penalty for a gap */
#define  DINS1     1       /* penalty per base */
#define  PINS0     8       /* penalty for a gap */
define  PINS1     4       /* penalty per residue */ struct jmp {
        short          n[MAXJMP];      /* size of jmp (neg for dely) */
        unsigned short x[MAXJMP];      /* base no. of jmp in seq x */
};                                      /* limits seq to 2^16 -1 */ struct diag {
        int            score;          /* score at last jmp */
        long           offset;         /* offset of prev block */
        short          ijmp;           /* current jmp index */
        struct jmp     jp;             /* list of jmps */
};

struct path {
```

```
        int     spc;            /* number of leading spaces */
        short   n[JMPS];        /* size of jmp (gap) */
        int     x[JMPS];        /* loc of jmp (last elem before gap) */
};

char            *ofile;         /* output file name */
char            *namex[2];      /* seq names: getseqs() */
char            *prog;          /* prog name for err msgs */
char            *seqx[2];       /* seqs: getseqs() */
int             dmax;           /* best diag: nw() */
int             dmax0;          /* final diag */
int             dna;            /* set if dna: main() */
int             endgaps;        /* set if penalizing end gaps */
int             gapx, gapy;     /* total gaps in seqs */
int             len0, len1;     /* seq lens */
int             ngapx, ngapy;   /* total size of gaps */
int             smax;           /* max score: nw() */
int             *xbm;           /* bitmap for matching */
long            offset;         /* current offset in jmp file */
struct  diag    *dx;            /* holds diagonals */
struct  path    pp[2];          /* holds path for seqs */ char            *calloc(), *malloc(), *index(), *strcpy();
char            *getseq(), *g_calloc();
```

```
/* Needleman-Wunsch alignment program
 *
 * usage: progs file1 file2
 *  where file1 and file2 are two dna or two protein sequences.
 *  The sequences can be in upper- or lower-case an may contain ambiguity
 *  Any lines beginning with ';', '>' or '<' are ignored
 *  Max file length is 65535 (limited by unsigned short x in the jmp struct)
 *  A sequence with 1/3 or more of its elements ACGTU is assumed to be DNA
 *  Output is in the file "align.out"
 *
 *  The program may create a tmp file in /tmp to hold info about traceback.
 *  Original version developed under BSD 4.3 on a vax 8650
 */
include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                            main
        int     ac;
        char    *av[];
```

```
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;              /* 1 to penalize endgaps */
        ofile = "align.out";      /* output file */ nw();                     /* fill in the matrix, get the possible jmps */
        readjmps();               /* get the actual jmps */
        print();                  /* print stats, alignment */ cleanup(0);               /* unlink any tmp files */
}

/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                                                nw
{
        char        *px, *py;         /* seqs and ptrs */
        int         *ndely, *dely;    /* keep track of dely */
        int         ndelx, delx;      /* keep track of delx */
        int         *tmp;             /* for swapping row0, row1 */
        int         mis;              /* score for each type */
        int         ins0, ins1;       /* insertion penalties */
        register    id;               /* diagonal index */
        register    ij;               /* jmp index */
        register    *col0, *col1;     /* score for curr, last row */
        register    xx, yy;           /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely",  len1+1, sizeof(int));
        col0  = (int *)g_calloc("to get col0",  len1+1, sizeof(int));
        col1  = (int *)g_calloc("to get col1",  len1+1, sizeof(int));
        ins0  = (dna)? DINS0 : PINS0;
        ins1  = (dna)? DINS1 : PINS1;
```

```
smax = -10000;
if (endgaps) {
        for (col0[0] = dely[0] = -ins0, yy = 1; yy <= len1; yy++) {
                col0[yy] = dely[yy] = col0[yy-1] - ins1;
                ndely[yy] = yy;
        }
        col0[0] = 0;        /* Waterman Bull Math Biol 84 */
}
else
        for (yy = 1; yy <= len1; yy++)
                dely[yy] = -ins0;

/* fill in match matrix
 */
for (px = seqx[0], xx = 1; xx <= len0; px++, xx++) {
        /* initialize first entry in col
         */
        if (endgaps) {
                if (xx == 1)
                        col1[0] = delx = -(ins0+ins1);
                else
                        col1[0] = delx = col0[0] - ins1;
                ndelx = xx;
        }
        else {
                col1[0] = 0;
                delx = -ins0;
                ndelx = 0;
        }
```

...nw

```
        for (py = seqx[1], yy = 1; yy <= len1; py++, yy++) {
                mis = col0[yy-1];
                if (dna)
                        mis += (xbm[*px-'A']&xbm[*py-'A'])? DMAT : DMIS;
                else
                        mis += _day[*px-'A'][*py-'A'];

/* update penalty for del in x seq;
                 * favor new del over ongong del
                 * ignore MAXGAP if weighting endgaps
                 */
                if (endgaps || ndely[yy] < MAXGAP) {
                        if (col0[yy] - ins0 >= dely[yy]) {
                                dely[yy] = col0[yy] - (ins0+ins1);
                                ndely[yy] = 1;
                        } else {
                                dely[yy] -= ins1;
                                ndely[yy]++;
                        }
                } else {
                        if (col0[yy] - (ins0+ins1) >= dely[yy]) {
                                dely[yy] = col0[yy] - (ins0+ins1);
                                ndely[yy] = 1;
                        } else
                                ndely[yy]++;
                }

/* update penalty for del in y seq;
```

```
             * favor new del over ongong del
             */
            if (endgaps || ndelx < MAXGAP) {
                    if (col1[yy-1] - ins0 > = delx) {
                            delx = col1[yy-1] - (ins0+ins1);
                            ndelx = 1;
                    } else {
                            delx -= ins1;
                            ndelx++;
                    }
            } else {
                    if (col1[yy-1] - (ins0+ins1) > = delx) {
                            delx = col1[yy-1] - (ins0+ins1);
                            ndelx = 1;
                    } else
                            ndelx++;
            }

/* pick the maximum score; we're favoring
             * mis over any del and delx over dely
             */
```

...nw

```
            id = xx - yy + len1 - 1;
            if (mis > = delx && mis > = dely[yy])
                    col1[yy] = mis;
            else if (delx > = dely[yy]) {
                    col1[yy] = delx;
                    ij = dx[id].ijmp;
                    if (dx[id].jp.n[0] && (!dna || (ndelx > = MAXJMP
                        && xx > dx[id].jp.x[ij]+MX) || mis > dx[id].score+DINS0)) {
                            dx[id].ijmp++;
                            if (++ij > = MAXJMP) {
                                    writejmps(id);
                                    ij = dx[id].ijmp = 0;
                                    dx[id].offset = offset;
                                    offset += sizeof(struct jmp) + sizeof(offset);
                            }
                    }
                    dx[id].jp.n[ij] = ndelx;
                    dx[id].jp.x[ij] = xx;
                    dx[id].score = delx;
            }
            else {
                    col1[yy] = dely[yy];
                    ij = dx[id].ijmp;
    if (dx[id].jp.n[0] && (!dna || (ndely[yy] > = MAXJMP
                        && xx > dx[id].jp.x[ij]+MX) || mis > dx[id].score+DINS0)) {
                            dx[id].ijmp++;
                            if (++ij > = MAXJMP) {
                                    writejmps(id);
                                    ij = dx[id].ijmp = 0;
                                    dx[id].offset = offset;
                                    offset += sizeof(struct jmp) + sizeof(offset);
```

```
                        }
                }
                dx[id].jp.n[ij] = -ndely[yy];
                dx[id].jp.x[ij] = xx;
                dx[id].score = dely[yy];
        }
        if (xx == len0 && yy < len1) {
                /* last col
                */
                if (endgaps)
                        col1[yy] -= ins0+ins1*(len1-yy);
                if (col1[yy] > smax) {
                        smax = col1[yy];
                        dmax = id;
                }
            }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
    }
    (void) free((char *)ndely);
    (void) free((char *)dely);
    (void) free((char *)col0);
    (void) free((char *)col1);                              }

/*
*
* print() -- only routine visible outside this module
*
* static:
* getmat() -- trace back best path, count matches: print()
* pr_align() -- print alignment of described in array p[]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/ include "nw.h"

define SPC     3
#define P_LINE  256     /* maximum output line */
define P_SPC   3       /* space between name or num and seq */ extern  _day[26][26];
int     olen;           /* set output line length */
FILE    *fx;            /* output file */ print()
{
        int     lx, ly, firstgap, lastgap;      /* overlap */ if ((fx = fopen(ofile, "w")) == 0) {
                fprintf(stderr,"%s: can't write %s\n", prog, ofile);
```

```
        cleanup(1);
}
fprintf(fx, "<first sequence: %s (length = %d)\n", namex[0], len0);
fprintf(fx, "<second sequence: %s (length = %d)\n", namex[1], len1);
olen = 60;
lx = len0;
ly = len1;
firstgap = lastgap = 0;
if (dmax < len1 - 1) {         /* leading gap in x */
        pp[0].spc = firstgap = len1 - dmax - 1;
        ly -= pp[0].spc;
}
else if (dmax > len1 - 1) {    /* leading gap in y */
        pp[1].spc = firstgap = dmax - (len1 - 1);
        lx -= pp[1].spc;
}
if (dmax0 < len0 - 1) {        /* trailing gap in x */
        lastgap = len0 - dmax0 -1;
        lx -= lastgap;
}
else if (dmax0 > len0 - 1) {   /* trailing gap in y */
        lastgap = dmax0 - (len0 - 1);
        ly -= lastgap;
}
getmat(lx, ly, firstgap, lastgap);
pr_align();
}

/*
* trace back the best path, count matches
*/
static
getmat(lx, ly, firstgap, lastgap)
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
``` getmat

```
        }
        else if (siz1) {
                p0++;
                n0++;
                siz1--;
        }
        else {
                if (xbm[*p0-'A']&xbm[*p1-'A'])
                        nm++;
                if (n0++ == pp[0].x[i0])
                        siz0 = pp[0].n[i0++];
                if (n1++ == pp[1].x[i1])
                        siz1 = pp[1].n[i1++];
                p0++;
                p1++;
        }
}

/* pct homology:
 * if penalizing endgaps, base is the shorter seq
 * else, knock off overhangs and take shorter core
 */
if (endgaps)
        lx = (len0 < len1)? len0 : len1;
else
        lx = (lx < ly)? lx : ly;
pct = 100.*(double)nm/(double)lx;
fprintf(fx, "\n");
fprintf(fx, " <%d match%s in an overlap of %d: %.2f percent similarity\n",
        nm, (nm == 1)? "" : "es", lx, pct);

fprintf(fx, " <gaps in first sequence: %d", gapx);
if (gapx) {
        (void) sprintf(outx, " (%d %s%s)",
                ngapx, (dna)? "base":"residue", (ngapx == 1)? "":"s");
        fprintf(fx,"%s", outx);
} fprintf(fx, ", gaps in second sequence: %d", gapy);
if (gapy) {
        (void) sprintf(outx, " (%d %s%s)",
                ngapy, (dna)? "base":"residue", (ngapy == 1)? "":"s");
        fprintf(fx,"%s", outx);
}
if (dna)
        fprintf(fx,
        "\n<score: %d (match = %d, mismatch = %d, gap penalty = %d + %d per base)\n",
        smax, DMAT, DMIS, DINS0, DINS1);
else
        fprintf(fx,
        "\n<score: %d (Dayhoff PAM 250 matrix, gap penalty = %d + %d per residue)\n",
        smax, PINS0, PINS1);
if (endgaps)
        fprintf(fx,
        "<endgaps penalized. left endgap: %d %s%s, right endgap: %d %s%s\n",
        firstgap, (dna)? "base" : "residue", (firstgap == 1)? "" : "s",
        lastgap, (dna)? "base" : "residue", (lastgap == 1)? "" : "s");
else
```

...getmat

```
                fprintf(fx, "<endgaps not penalized\n");
} static          nm;               /* matches in core -- for checking */
static          lmax;             /* lengths of stripped file names */
static          ij[2];            /* jmp index for a path */
static          nc[2];            /* number at start of current line */
static          ni[2];            /* current elem number -- for gapping */
static          siz[2];
static char     *ps[2];           /* ptr to current element */
static char     *po[2];           /* ptr to next output char slot */
static char     out[2][P_LINE];   /* output line */
static char     star[P_LINE];     /* set by stars() */

/*
* print alignment of described in struct path pp[]
*/
static
pr_align()
{
        int         nn;    /* char count */
        int         more;
        register    i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];                } for (nn = nm = 0, more = 1; more; ) {
                for (i = more = 0; i < 2; i++) {
                        /*
                        * do we have more of this sequence?
                        */
                        if (!*ps[i])
                                continue;

more++;

if (pp[i].spc) {    /* leading space */
                                *po[i]++ = ' ';
                                pp[i].spc--;
                        }
                        else if (siz[i]) {  /* in a gap */
                                *po[i]++ = '-';
                                siz[i]--;
                        }
                        else {              /* we're putting a seq element
                                            */
                                *po[i] = *ps[i];
                                if (islower(*ps[i]))
                                        *ps[i] = toupper(*ps[i]);
``` pr_align

...pr_align

```
                    po[i]++;
                    ps[i]++;

/*
                     * are we at next gap for this seq?
                     */
                    if (ni[i] == pp[i].x[ij[i]]) {
                        /*
                         * we need to merge all gaps
                         * at this location
                         */
                        siz[i] = pp[i].n[ij[i]++];
                        while (ni[i] == pp[i].x[ij[i]])
                            siz[i] += pp[i].n[ij[i]++];
                    }
                    ni[i]++;
                }
            }
            if (++nn == olen || !more && nn) {
                dumpblock();
                for (i = 0; i < 2; i++)
                    po[i] = out[i];
                nn = 0;
            }
        }
    }
}
/*
 * dump a block of lines, including numbers, stars: pr_align()
 */
static
dumpblock()
{
        register i;

for (i = 0; i < 2; i++)
                *po[i]-- = '\0';
``` dumpblock

```
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars();
                        putline(i);
                        if (i == 0 && *out[1])
                                fprintf(fx, star);
                        if (i == 1)
                                nums(i);
                }
        }
}
/*
 * put out a number line: dumpblock()
 */
static
```

...dumpblock

```
nums(ix)
        int         ix;         /* index in out[] holding seq line */
{
        char        nline[P_LINE];
        register    i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
 * put out a line (name, [num], seq, [num]): dumpblock()
 */
static
putline(ix)
        int         ix;         { int         i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
``` nums putline

...putline

```
* put a line of stars (seqs always in out[0], out[1]): dumpblock()
*/
static
stars()                                                                          stars
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}

/*
 * strip path or prefix from pn, return len: pr_align()
 */
static
stripname(pn)                                                                    stripname
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
```

```
/*
*  cleanup()  -- cleanup any tmp file
*  getseq()   -- read in seq, set dna, len, maxlen
*  g_calloc() -- calloc() with error checkin
*  readjmps() -- get the good jmps, from tmp file if necessary
*  writejmps() -- write a filled array of jmps to a tmp file: nw()
*/
include "nw.h"
include <sys/file.h> char    *jname = "/tmp/homgXXXXXX";         /* tmp file for jmps */
FILE    *fj;

int     cleanup();                          /* cleanup tmp file */
long    lseek();

/*
* remove any tmp file if we blow
*/
cleanup(i)
        int     i;
{
        if (fj)
                (void) unlink(jname);
        exit(i);
}
```
cleanup

```
/*
* read, return ptr to seq, set dna, len, maxlen
* skip lines starting with ';', '<', or '>'
* seq in upper or lower case
*/
char    *
getseq(file, len)
        char    *file;      /* file name */
        int     *len;       /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```
getseq

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
``` g_calloc

```
char    *
g_calloc(msg, nx, sz)
        char    *msg;           /* program, calling routine */
        int     nx, sz;         /* number and size of elements */
{
        char            *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}
```

```
/*
 * get final jmps from dx[] or tmp file, set pp[], reset dmax: main()
 */
readjmps()
``` readjmps

```
{
        int             fd = -1;
        int             siz, i0, i1;
        register        i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
```

```
                    while (1) {
                            for (j = dx[dmax].ijmp; j >= 0 && dx[dmax].jp.x[j] >= xx; j--)
                                    ;
```
...readjmps
```
                            if (j < 0 && dx[dmax].offset && fj) {
                                    (void) lseek(fd, dx[dmax].offset, 0);
                                    (void) read(fd, (char *)&dx[dmax].jp, sizeof(struct jmp));
                                    (void) read(fd, (char *)&dx[dmax].offset, sizeof(dx[dmax].offset));
                                    dx[dmax].ijmp = MAXJMP-1;
                            }
                            else
                                    break;
                    }
                    if (i >= JMPS) {
                            fprintf(stderr, "%s: too many gaps in alignment\n", prog);
                            cleanup(1);
                    }
                    if (j >= 0) {
                            siz = dx[dmax].jp.n[j];
                            xx = dx[dmax].jp.x[j];
                            dmax += siz;
                            if (siz < 0) {                    /* gap in second seq */
                                    pp[1].n[i1] = -siz;
                                    xx += siz;
                                    /* id = xx - yy + len1 - 1
                                    */
                                    pp[1].x[i1] = xx - dmax + len1 - 1;
                                    gapy++;
                                    ngapy -= siz;
/* ignore MAXGAP when doing endgaps */
                                    siz = (-siz < MAXGAP || endgaps)? -siz : MAXGAP;
                                    i1++;
                            }
                            else if (siz > 0) {    /* gap in first seq */
                                    pp[0].n[i0] = siz;
                                    pp[0].x[i0] = xx;
                                    gapx++;
                                    ngapx += siz;
/* ignore MAXGAP when doing endgaps */
                                    siz = (siz < MAXGAP || endgaps)? siz : MAXGAP;
                                    i0++;
                            }
                    }
                    else
                            break;
            }
            /* reverse the order of jmps
            */
            for (j = 0, i0--; j < i0; j++, i0--) {
                    i = pp[0].n[j]; pp[0].n[j] = pp[0].n[i0]; pp[0].n[i0] = i;
                    i = pp[0].x[j]; pp[0].x[j] = pp[0].x[i0]; pp[0].x[i0] = i;
            }
            for (j = 0, i1--; j < i1; j++, i1--) {
                    i = pp[1].n[j]; pp[1].n[j] = pp[1].n[i1]; pp[1].n[i1] = i;
                    i = pp[1].x[j]; pp[1].x[j] = pp[1].x[i1]; pp[1].x[i1] = i;
            }
            if (fd >= 0)
                    (void) close(fd);
```

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "hepatocyte growth factor" or "HGF", as used herein, refers to any native or variant (whether native or synthetic) HGF polypeptide that is capable of inducing at least one, preferably all, steps in the multi-stage angiogenic process under conditions that permit such process to occur. Many agonists of HGF are known in the art, including HGF polypeptide variants (such as deletion mutants comprising less than the complete form/amino acid sequence of native HGF protein, the delta5 variant (see, for e.g., Miyazawa et al., Biochem. Biophys. Res. Comm. (1989), 163:967-973; Nakamura et al., Nature (1989), 342:440-443; Seki et al., Biochem. and Biophys. Res. Commun. (1990), 172:321-327; Tashiro et al., Proc. Natl. Acad. Sci. U.S.A. (1990), 87:3200-3204; Okajima et al., Eur. J. Biochem. (1990), 193:375-381; U.S. Pat. No. 5,547,856)) and agonist antibodies (such as those described in U.S. Pat. No. 6,099,841).

Any term referring to a growth factor, angiogenic and other polypeptides as used herein refers to any native or variant (whether native or synthetic) of the polypeptide that is capable of effecting at least one of the biological functions/ activities of the native polypeptide, said functions/activities being readily discernible in the context of the description of its use. Thus, for e.g., the term VEGF or bFGF would refer to a native or variant form of the VEGF or bFGF protein, respectively, that retains the capability of inducing at least one, preferably all, steps in the multi-stage angiogenic process under conditions that permit such process to occur.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen (preferably STC-1, which is preferably mammalian STC-1, which is preferably human STC-1). In another embodiment, an antibody fragment, for example one that comprises at least a portion of the Fc region, retains at least one of the biological functions normally associated with the Fc region when present in an intact antibody, such as FcRn binding, antibody half life modulation, ADCC function and complement binding.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and *Gross, Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technoloy* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds (which is preferably STC-1 or variant thereof as described herein). Preferred blocking antibodies or antagonist antibodies substantially or completely inhibit the biological activity of the antigen.

An "agonist antibody", as used herein, is an antibody which mimics at least one of the functional activities of STC-1, in particular with respect to the modulatory activity of STC-1 in angiogenesis.

A "disorder" is any condition that would benefit from treatment with a polypeptide or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, polypeptides, polynucleotides, agonist and/or antagonist molecules (such as antibodies) of the invention are used to delay development of a disease or disorder.

An "effective amount" refers to an amount effective, at dosages and for periods of time necessary, to achieve the desired therapeutic or prophylactic result. A "therapeutically effective amount" of STC-1, agonist or antagonist may vary according to factors such as the disease state, age, sex, and weight of the individual, and the ability of the STC-1, agonist or antagonist to elicit a desired response in the individual. A therapeutically effective amount is also one in which any toxic or detrimental effects of the STC-1, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Vector Construction

Polynucleotide sequences encoding the polypeptides of the invention (including STC-1, antibodies) can be obtained using standard recombinant techniques. Desired polynucleotide sequences may be isolated and sequenced from appropriate source cells, for example as illustrated in the Examples below. Source cells for antibodies would include antibody producing cells such as hybridoma cells. Alternatively, polynucleotides can be synthesized using nucleotide synthesizer or PCR techniques. Once obtained, sequences encoding the immunoglobulins are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, $E.\ coli$ is typically transformed using pBR322, a plasmid derived from an $E.\ coli$ species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as $E.\ coli$ LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide of the invention (e.g., STC-1, antibodies) by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

Prokaryotic host cells suitable for expressing polypeptides include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*),

*Salmonella typhimurium, Serratia marcescans, Klebsiella, Proteus, Shigella, Rhizobia, Vitreoscilla,* or *Paracoccus*. Preferably, gram-negative cells are used. Preferably the host cell should secrete minimal amounts of proteolytic enzymes, and additional protease inhibitors may desirably be incorporated in the cell culture.

Polypeptide Production

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Polypeptides of the present invention expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Polypeptide Purification

Polypeptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Methods of the Invention

The invention provides various methods based on the finding that STC-1 selectively modulates certain but not all aspects of angiogenesis. For example, the invention provides methods of diagnosis, such as tissue typing, wherein STC-1 may be differentially expressed in one tissue as compared to another, preferably in a diseased tissue as compared to a normal tissue of the same tissue type.

STC-1 polypeptides described herein may also be employed as therapeutic agents. These polypeptides can be formulated according to known methods to prepare pharmaceutically useful compositions, whereby the polypeptide product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a polypeptide is desired in a formulation with release characteristics suitable for the treatment of any disease or disorder requiring administration of the polypeptide, microencapsulation of the polypeptide is contemplated. Microencapsulation of recombinant proteins for sustained release has been successfully performed with human growth hormone (rhGH), interferon-(rhIFN—), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic STC-1 (agonists) or prevent the effect of STC-1 (antagonists). Screening assays for antagonist drug candidates are designed to identify compounds that bind or complex with the STC-1 polypeptides, or otherwise interfere with the interaction of STC-1 with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with an STC-1 polypeptide under conditions and for a time sufficient to allow these two components to interact.

In binding assays, the interaction is binding and the complex formed can be isolated or detected in the reaction mixture. In a particular embodiment, an STC-1 polypeptide or the drug candidate is immobilized on a solid phase, e.g., on a microtiter plate, by covalent or non-covalent attachments. Non-covalent attachment generally is accomplished by coating the solid surface with a solution of the immobilized component (for e.g., STC-1 polypeptide) and drying. Alternatively, an immobilized antibody, e.g., a monoclonal antibody, specific for the component to be immobilized (for e.g., STC-1 polypeptide) can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a STC-1 polypeptide, its interaction with the polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a STC-1 polypeptide and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between, the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the STC-1 polypeptide may be added to a cell along with the compound to be screened for a particular activity and the ability of the compound to inhibit the activity of interest in the presence of the STC-1 polypeptide indicates that the compound is an antagonist to the STC-1 polypeptide. To assay for agonists, a candidate agonist compound can be contacted with a cell known to respond to the STC-1 polypeptide, and assessed for an activity associated with the STC-1 polypeptide. The assay could also be performed in the presence of the STC-1 polypeptide itself to assess ability of the candidate compound to enhance the activity of STC-1.

More specific examples of potential agonists and antagonists include antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the STC-1 polypeptide that recognizes an STC-1 binding partner but imparts no effect, thereby competitively inhibiting the action of the STC-1 polypeptide.

Another potential STC-1 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the STC-1 polypeptide, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the STC-1 polypeptide. The antisense RNA oligonucleotide hybridizes to the mRNA in vivo and blocks translation of the mRNA molecule into the STC-1 polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the STC-1 polypeptide. When antisense DNA is used, oligodeoxyribonucleotides derived from the translation-initiation site, e.g., between about −10 and +10 positions of the target gene nucleotide sequence, are preferred.

Potential agonists and antagonists include small molecules that bind to the active site, the binding site of STC-1 on another molecule, or other relevant binding site of the STC-1 polypeptide, thereby mimicking, enhancing or blocking the normal biological activity of the STC-1 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Anti-STC-1 Antibodies

The present invention provides methods comprising use of anti-STC-1 antibodies. Exemplary antibodies include polyclonal, monoclonal, humanized, bispecific, and heteroconjugate antibodies.

1. Polyclonal Antibodies

The anti-STC-1 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the STC-1 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-STC-1 antibodies may, alternatively and preferably, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the STC-1 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against STC-1. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Antibodies can also be generated by screening phage display libraries for antibodies or antibody fragments that bind with suitable/desired affinity to a target antigen such as STC-1 or an STC-1 variant. Such techniques are well known in the art, for e.g., as disclosed in U.S. Pat. Nos. 5,750,373; 5,780,279; 5,821,047; 6,040,136; 5,427,908; 5,580,717, and references therein.

3. Human and Humanized Antibodies

The anti-STC-1 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities can be for the STC-1 polypeptide, the other one can be for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a STC-1 polypeptide herein. Alternatively, an anti-STC-1 polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing STC-1. Bispecific antibodies may also be used to localize cytotoxic agents to cells which express the STC-1 polypeptide. These antibodies possess a STC-1 binding arm and an arm which binds a cytotoxic agent or a radionuclide chelator, such as EOTUBE, DPTA, DOTA, or TETA. Another bispecific antibody of interest binds the STC-1 polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.,* 176: 1191-1195 (1992) and Shopes, *J. Immunol.,* 148: 2918-2922 (1992). Homodimeric antibodies with enhanced anti-tumor activity may also be prepared using heterobifunctional cross-linkers as described in Wolff et al. *Cancer Research,* 53: 2560-2565 (1993). Alternatively, an antibody can be engineered that has dual Fc regions and may thereby have enhanced complement lysis and ADCC capabilities. See Stevenson et al., *Anti-Cancer Drug Design,* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

9. Compositions of Antibodies

Antibodies specifically binding STC-1 polypeptide, as well as other molecules identified by the screening assays disclosed hereinbefore, can be administered for the treatment of various disorders in the form of compositions, wherein in some embodiments the compositions also comprise a carrier (for e.g., a pharmaceutically acceptable carrier).

If the STC-1 polypeptide is to be targeted intracellularly and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences,* supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The following are examples of the methods and compositions of the invention. It is understood that various other embodiments may be practiced, given the general description provided above.

EXAMPLES

Example 1

Materials and Methods

Reagents: Human umbilical vein endothelial cells (HUVECs) were purchased from Clonetics (San Diego, Calif.) and maintained in Endothelial Growth Medium (EGM) (Clonetics) supplemented to a final concentration of 10% fetal bovine serum. Other reagents included type 1 rat tail collagen (Upstate Biotechnology. Lake Success, N.Y.), recombinant bFGF (Collaborative Biomedical Products, Bedford, Mass.), recombinant VEGF and HGF (Genentech, South San Francisco, Calif.). All other cell culture reagents were from Gibco-BRL (Gaithersburg, Md.).

Isolation of STC-1 and Construction of Expression Vectors: cDNA clones were isolated from a human endothelial cDNA library and sequenced in their entirety. Fc fusion proteins (immunoadhesins) were prepared by fusion of the entire open reading frame of STC-1 in frame with the Fc region of human IgG1 using the baculovirus vector pHIF, a derivative of pVL1393 purchased from Pharmingen. Fusion proteins were transiently expressed in Sf9 insect cells and purified over a protein A column. STC-1 was also expressed as a C-terminal His tag fusion in *Escherichia coli* and the denatured protein used for immunization. The identities of the purified proteins were verified by N-terminal sequence analysis.

Preparation of monoclonal antibodies to STC-1: Ten Balb/c mice (Charles River Laboratories, Wilmington, Del.) were hyperimmunized with recombinant polyhistidine-tagged (HIS8) human STC-1 expressed in *E. coli* (Genentech, Inc. South San Francisco, Calif.) in Ribi adjuvant (Ribi Immunochem Research, Inc., Hamilton, Mo.). B-cells from five mice demonstrating high anti-STC-1 antibody titers were fused with mouse myeloma cells (X63.Ag8.653; American Type Culture Collection, Rockville, Md.) using a modified protocol analogous to one previously described (3,4). After 10-14 days, the supernatants were harvested and screened for antibody production by direct enzyme-linked immunosorbent assay (ELISA). Five positive clones, showing the highest immunobinding after the second round of subcloning by limiting dilution, were injected into Pristaneprimed mice (5) for in vivo production of MAb. The ascites fluids were pooled and purified by Protein A affinity chromatography (Pharmacia fast protein liquid chromatography [FPLC]; Pharmacia, Uppsala, Sweden) as previously described (3). The purified antibody preparations were sterile filtered (0.2-μm pore size; Nalgene, Rochester N.Y.) and stored at 4° C. in phosphate buffered saline (PBS).

Antibody clones were deposited with the ATCC under the Budapest Treaty. American Type Culture Collection (ATCC) is located at 10801 University Boulevard, Manassas, Va. 20110-2209. Details of the deposits are as follows:

| Clone designation | Deposit Date | ATCC Deposit No. |
|---|---|---|
| 3E10.1F5.1D11 | Mar. 28, 2003 | PTA-5100 |
| 21F4.2F11.1H12 | Mar. 28, 2003 | PTA-5103 |
| 1F10.2F12.1E7 | Mar. 28, 2003 | PTA-5101 |
| 18F1.1E6.1B10 | Mar. 28, 2003 | PTA-5099 |
| 12C3.2F3.2D8 | Mar. 28, 2003 | PTA-5102 |

ELISA for STC-1: High-binding, flat-bottom polypropylene 96-well plates (NUNC, Naperville, Ill.) were coated overnight at 4° C. with 100 μL monoclonal STC-1 antibody 2734 (clone 21F4.2F11.1H12, ATCC Deposit No. PTA-5103) (250 ng/mL). The plates were washed (PBS containing 0.05% Tween), blocked (PBS containing 0.5% BSA), and washed again before adding 100 μL of supernatant or STC-1 onto duplicate wells. After subsequent washing steps, a second biotinylated STC-1 monoclonal antibody (2733 (clone 12C3.2F3.2D8, ATCC Deposit No. PTA-5102); 250 ng/mL) was added to the wells. After 2 hr incubation and a wash step, a 1:10,000 dilution of Streptavidin-HRP (Amersham, Gaithersburg, Md.) was added to the plates. Tetramethyl benzidine (TMB, Kirkegaard & Perry, Gaithersburg, Md.) was added followed by 1 M phosphoric acid and the absorbance at 450 nm determined (Spectra Max 250 Molecular Devices, Sunnyvale, Calif.). The minimum level of STC-1 that could be reliably detected by the ELISA was 20 pg/mL.

RNA Isolation and Quantitative Reverse Transcriatase-Polymerase Chain Reaction (Tagman): Tri-Reagent-LS (Molecular Research Center, Cincinnati, Ohio) was added to the cells and total RNA was extracted according to manufacturer's protocols. Gene-specific oligonucleotide primer pairs and a specific probe (labeled with a fluorescent dye at the 5' end and a quencher fluorescent dye at the 3' end) were designed using Oligo 4.0 software (National Biosciences, Plymouth, Minn.) and levels of STC-1 mRNA determined by real time quantitative PCR (Tagman) as previously described (6). Sequences for primers and probe were as described in Table 1 (under Gene name "Stanniocalcin precursor") of Kahn et al., Am. J. Pathology (2000), 156(6):1887-1900.

Western Blotting: Equal amounts of supernatants were denatured and loaded onto 10% Tris-Glycine gels. Following electrophoresis, the proteins were transferred to nitrocellulose membranes using a Panther HEP-3 semi-dry blotter (Owl Scientific Separations-Daigger, Vernon Hills Ill.). STC-1 was detected using STC-1 antibody 2734 (clone 21F4.2F11.1H12, ATCC Deposit No. PTA-5103) and the ECL detection method (Amersham Pharmacia, Piscataway).

Culture of Cells: HUVECs were routinely grown on gelatin (1 µg/mL) coated plates in EGM media. Drugs and growth factors were added to the media and prewarmed to 37° C. before addition to the HUVECs. Collagen gels containing HUVECs were prepared as described previously (1). The gels were overlaid with 1× basal media (Medium 199 supplemented with 1% fetal bovine serum, 1% ITS (Insulin, selenium and transferring, source) 2 mM L-glutamine) and 100 U/mL penicillin, and 100 U/mL streptomycin) containing 200 ng/mL HGF and 200 ng/mL VEGF to elicit tube formation as previously described (1). For "film" experiments endothelial cells were seeded on the surface of a collagen gel and incubated in the identical media as that described for the gel experiments. To evaluate endothelial morphogenesis on Matrigel (Collaborative Research, Bedford, Mass.), cells were incubated in 1× basal media in the presence of various factors as described. Network formation was quantitated at 8 hours by photographing 3 random fields of each well, then determining the total network area per field using Openlab 2.5 software (Improvision, Bedford, Mass.).

Cell Migration Assay: HTS multiwell insert 24 well plates (BD Biosciences, Bedford, Mass.) were coated with cell attachment factor (BD Biosciences) on the bottom layer and type 1 collagen on the membrane surface. 25,000 cells were seeded into each chamber and incubated for 18 h at 37° C./5% $CO_2$. The collagen and unmigrated cells were scraped off the membrane surface with a plastic pasteur pipette and then all media was aspirated. Absolute methanol was added to the membrane and membranes fixed at room temperature for 30 minutes. The methanol was aspirated off and a 10 µM solution of YO-PRO-1 (Molecular Probes, Eugene, Oreg.) was added. Cells were counted under FITC optics using OpenLab 2.5.

Proliferation Assay: 5,000 cells were seeded onto gelatin coated 96 well plates and incubated overnight with EGM. The cells were then starved for 3 days with M199 containing 1% FBS, 2 mmol/L L-glutamine, 100 U/mL penicillin, and 100 U/mL streptomycin. 20 ng/mL of various growth factors were added to the starvation media and the cells were incubated for 4 days. Alamar blue solution (Biosource International, Camarillo, Calif.) was added to the wells in an amount equal to 10% of the culture volume and incubated for 4-6 hours at 37° C./5% $CO_2$. The plates were read on a Spectra Max Gemini (Molecular Devices, Sunnyvale, Calif.) with the OD excitation at 535 nm and emission at 590 nm.

Femoral Ligation Surgery: Femoral artery ligation was performed under Isoflurane (Aerrane, Fort Dodge) inhalation anesthesia on Male C57/BI6J mice (Charles River) (8-10 weeks). Briefly, the femoral artery was isolated at the level of the inguinal ligament and ligated with 7-0 silk suture (Ethicon, Somerville, N.J.). Animals were allowed to recover on a warm water heating pad until ambulatory. Total RNA was isolated from the gastrocnemius muscle of both the ligated and sham animals. Six animals were used for the control (sham) and six animals for the ligated group respectively for each time point.

Effects of STC-1 on HGF induced c-met phosphorylation: Confluent HYVEc were incubated overnight in Basal Medium. HUVEc monolayers were pretreated with native or boiled STC-1 (5 µg/ml) for 30 min in DME supplemented with 0.5% bovine serum albumin. HGF was then added (100 ng/ml) and cells incubated for 15 minute incubation at 37° C.

After addition of lysate buffer (PBS supplemented with 1% triton, protease inhibitor mix (Sigma) and phosphatase inhibitor mix (Sigma), lysates were immunoprecipitated with an antibody to c-met (C-28, Santa Cruise Biotechnology). Precipitates were resuspended in lysis buffer and loaded onto 10% Tris-Glycine gel, and western blots prepared as above. Phosphorylated c-met was detected with 4G10 (Upstate Biotechnology, N.Y.).

Data analysis: Numerical data are expressed as the mean ±SEM and the n for each experiment is provided in the figure legends or text. To determine statistical significance data were first evaluated by ANOVA, followed by Student's t-test for non-paired values. A p-value of <0.05 was accepted as significant.

Results

Regulation of STC-1 Production in Endothelial Cells in Monolayer Culture.

To evaluate the effects of various cytokines and growth factors on the release of STC-1 from HUVEC, we developed a ELISA based assay (see methods for details) which was capable of measuring STC-1 levels as low as 20 pg/ml. There was no detectable STC-1 release from unstimulated HUVEC (not shown). To survey for possible effects of various cytokines and growth factors on STC-1 release, confluent endothelial cells cultured in 96-well tissue culture plates were incubated with these factors for 24, 48 and 72 hours, and STC-1 levels determined in the cell supernatants. The majority of factors evaluated had either no effect (e.g. VEGF, TGFβ, bradykinin, histamine, and TNFα) or very modest effects (IL-1β) on STC-1 release at these time points. The concentrations shown in Table 1 are the highest concentration tested (for each drug we tested the indicated dose and at least two lower doses (e.g. 1:10 and 1:100) of that shown). Of the growth factors examined, only bFGF and HGF stimulated significant STC1 release. The cytokines IL-6 and IL-4 also stimulated STC-1 release.

TABLE 1

Effects of various agonists on the release of STC-1 by HUVEC. HUVEC monolayers were incubated with the indicated agonists and aliquots removed at 24, 48 and 72 hr and analyzed for STC-1 by ELISA. Data shown are the mean values (n = 4).

| | STC-1 (ng/ml) | | |
|---|---|---|---|
| Stimuli | 24 hr | 48 hr | 72 hr |
| Media | <.02 | <.02 | <.02 |
| Calcium Ionophore 10 mg/ml | <.02 | <.02 | ND |
| Bradykinin (1 µM) | <.02 | <.02 | ND |
| Histamine (1 µM) | <.02 | <.02 | ND |
| VEGF (400 ng/ml) | <.02 | <.02 | <.02 |
| TGF β (50 ng/ml) | <.02 | <.02 | <.02 |
| IFNγ (25 ng/ml) | <.02 | <.02 | <.02 |
| bFGF (400 ng/ml) | <.02 | <.02 | .092 |
| HGF (400 ng/ml) | <.02 | <.02 | .112 |
| TNFα (10 ng/ml) | <.02 | <.02 | .06 |
| IL-6 (25 ng/ml | <.02 | .023 | .114 |
| IL-1 (10 ng/ml) | <.02 | .027 | .027 |
| IL-4 25 ng/ml | <.02 | .025 | .122 |
| PMA (100 ng/ml) | .023 | .057 | .183 |

Figure 1B:
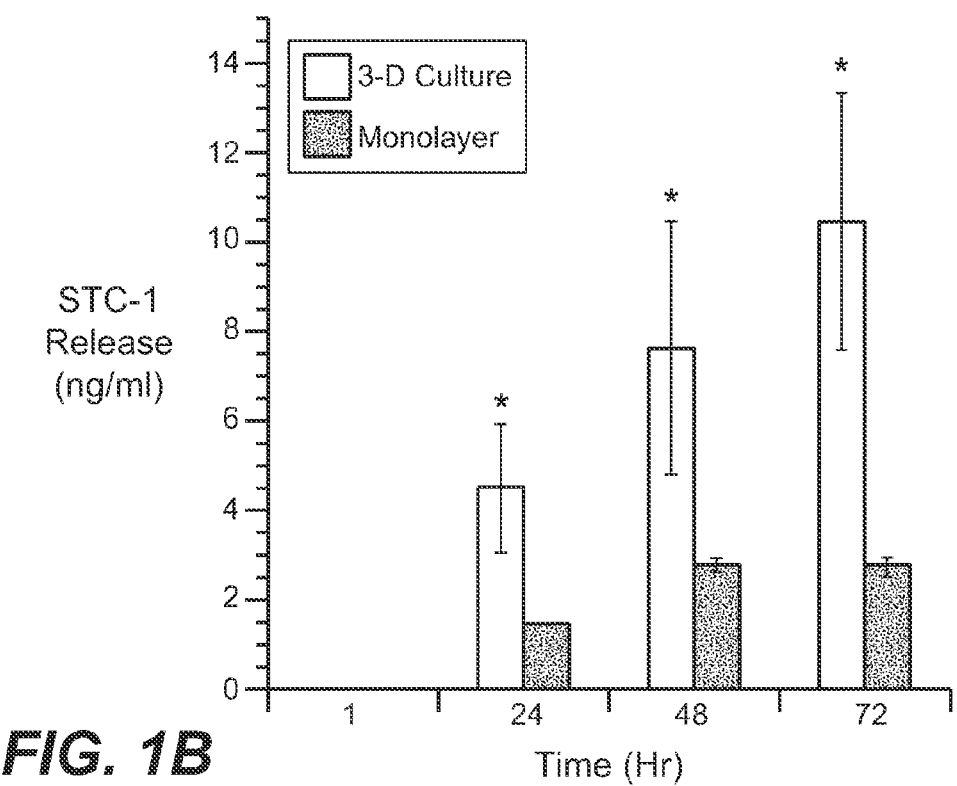

Levels of STC-1 mRNA and protein secretion are much greater in 3-D cultures compared to 2-D cultures. Equal numbers ($1.5 \times 10^7$) of HUVEc were plated either onto type I collagen gels ("film") or suspended in type I collagen gels (gel) and incubated with HGF and VEGF (200 ng/ml) for various times as indicated in FIG. 1. It should be noted that the combination of HGF and VEGF was required in 3D gels for survival-as described previously, neither growth factor alone was capable of supporting survival and tubulogenesis in 3D collagen gels (1). The mRNA levels (FIG. 1A) for STC-1 rose dramatically in the gel versus film environment, such that at 24 hr, the mRNA levels for STC-1 were 1020 fold higher in the 3-D cultures. Levels of STC-1 protein (FIG. 1B) in the supernatants were 2 to 6 fold higher in the 3-D compared to film cultures. Since the cells are embedded in 3D collagen gels, any protein in the supernatants must be "released" from the gel in order to be detected, and may account for the discrepancy in relative ratios of mRNA versus protein.

Effects of STC-1 on endothelial proliferation. STC-1 (0.001-1 μg/ml) had no effect on bFGF (10 ng/ml), VEGF (10 ng/ml) or HGF (10 ng/ml) stimulated endothelial proliferation (data not shown). Additionally, STC-1 did not stimulate endothelial proliferation when tested in the absence of growth factors (not shown).

Figure 2A:
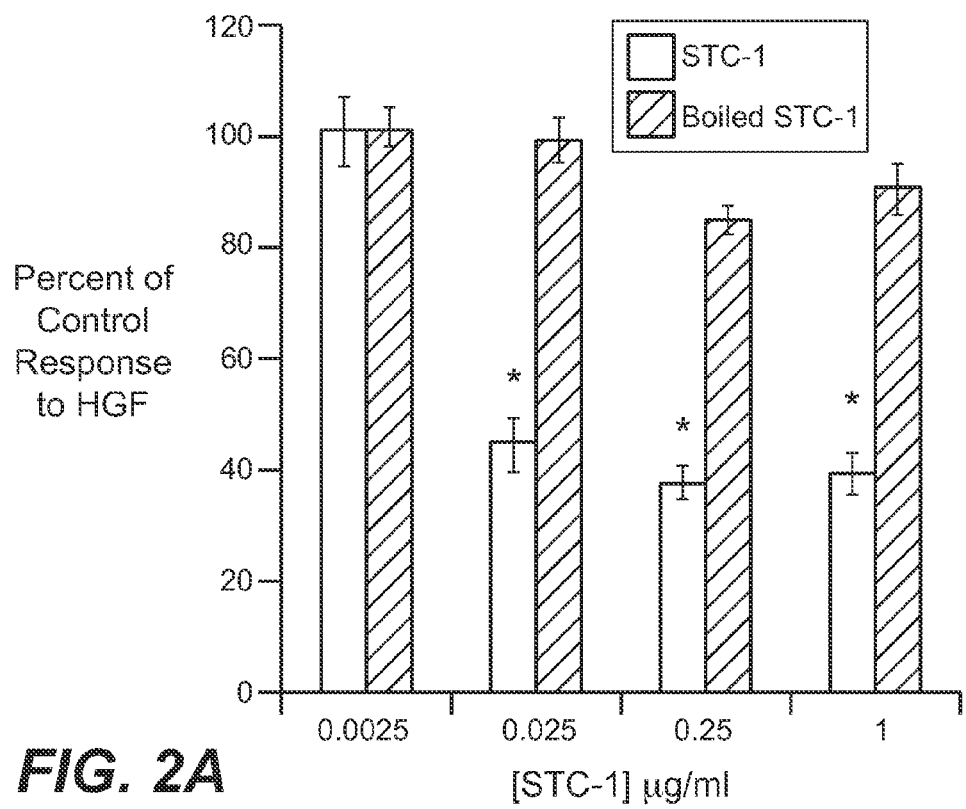
FIG. 2. STC-1 inhibits endothelial cell migration A. The migratory response of HUVEC to 20 ng/mL of HGF in the presence of native (solid bars) or boiled rSTC-1 (hatched bars) at the indicated concentrations was determined. Data are expressed as the percent of the HGF control cell migration index and are the mean ±S.E.M., n=4. Data shown are representative of three independent experiments. * Significantly different from HGF alone, p<0.05. B. The inhibitory effects of STC-1 on HGF (20 ng/mL)-induced migration are blocked by the monoclonal antibody 2734 (25 μg/mL) (produced by hybridoma clone 21F4.2F11.1H12, which has ATCC Deposit No. PTA-5103), but not by an isotype-matched nonimmune IgG. Data are expressed as cell migration index (number of cells/2× field) and are the mean ±S.E.M., n=4. Data shown are representative of three independent experiments. * Significantly different from control. ++ Significantly different from HGF alone, p<0.05.
Figure 2B:
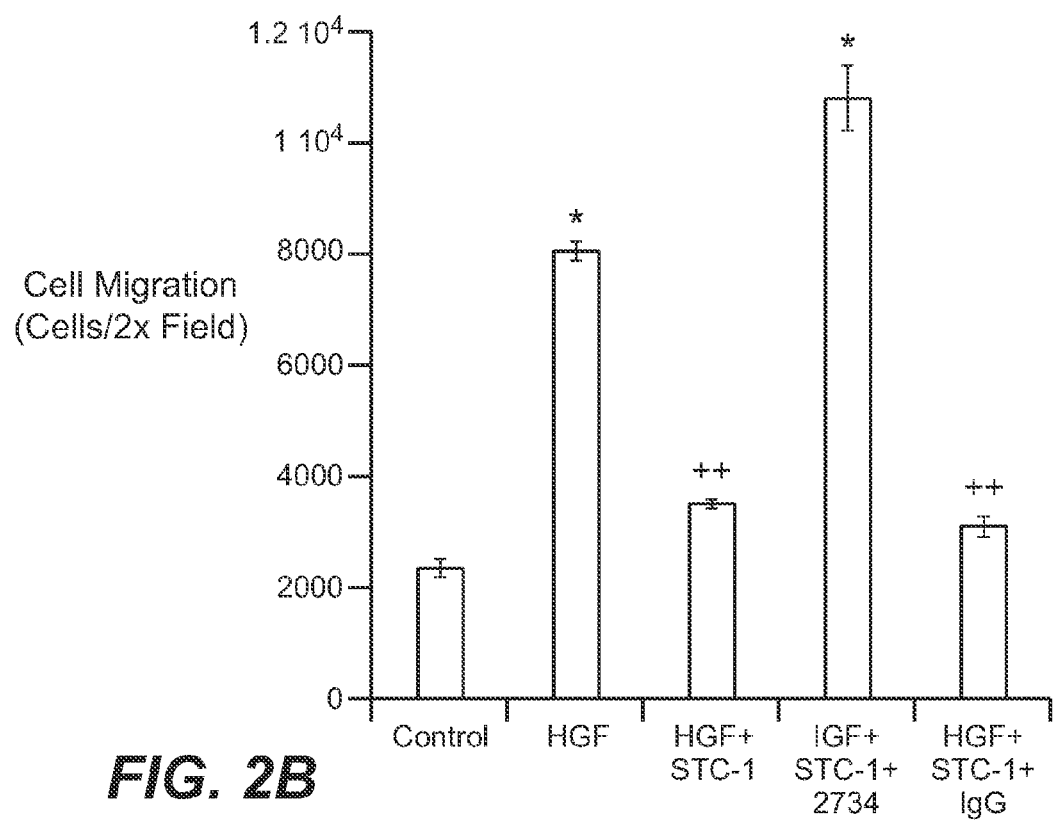

Effects of STC-1 on HGF induced endothelial migration: HGF is a known potent stimulus for endothelial migration. We, therefore, determined the role of STC-1 in HGF induced endothelial cell migration. As shown in FIG. 2A, rSTC1 (Ig fusion protein) when added to the Boyden chambers, markedly inhibited the migratory response of the endothelial cells to HGF. Denaturation of the recombinant protein by boiling completely eliminated this inhibitory activity. Additionally, the inhibitory effects of STC-1 were not observed at lower (2.5 ng/nL) concentrations of the protein. The inhibitory effects of STC-1 on HGF cell migration were also blocked by inclusion of 25 μg/mL of the anti-STC-1 monoloclonal antibody 2734 (clone 21F4.2F11.1H12, ATCC Deposit No. PTA-5103) (FIG. 2B) in contrast to the lack of effect of an isotype matched non-immune IgG. To further evaluate the selective effects of STC-1 on endothelial cell migration, we evaluated the effects of rSTC-1 on bFGF (10 ng/mL) and VEGF (10 ng/mL) induced endothelial cell migration. These doses of bFGF and VEGF elicited a similar magnitude of cell migration as 20 ng/mL HGF, yet none of the STC-1 reagents tested (native STC-1, boiled STC-1, STC1 monoclonal antibody 2734 (clone 21F4.2F11.1H12, ATCC Deposit No. PTA-5103) (25 μg/mL)) had a significant effect on the migratory response to bFGF or VEGF (data not shown).

Figure 3C:
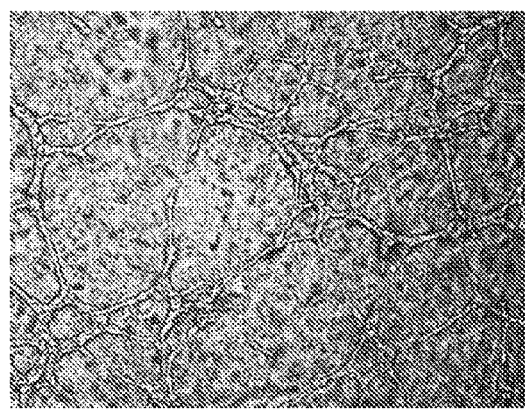
Figure 3C:
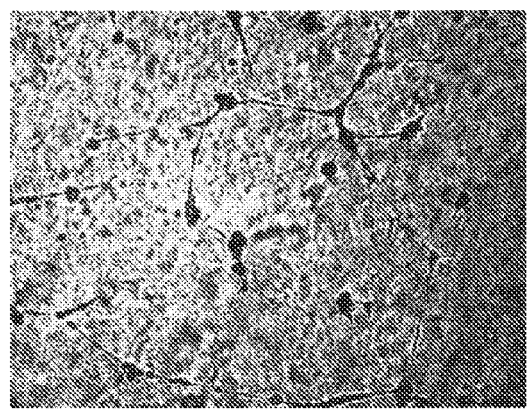
Figure 3C:
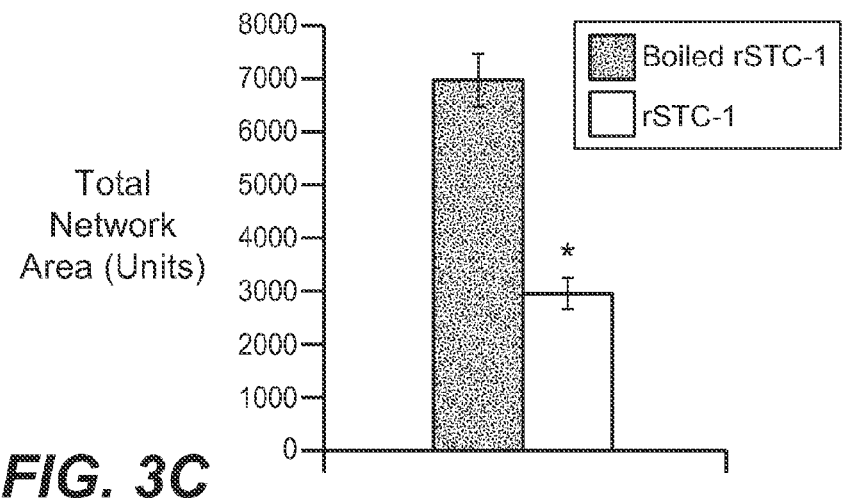

Effects of STC-1 on HGF induced endothelial morphogenesis To evaluate the possible effects of STC-1 on endothelial morphogenesis, we tested the effects of native rSTC-1 and boiled STC-1 on HGF induced endothelial branching network formation on growth factor depleted Matrigel. In this model, incubation of endothelial cells without a growth factor such as HGF results in little or no cord formation (not shown). Addition of HGF (20 ng/ml) results in an elaborate network of endothelial branching structures (FIG. 3A). Addition of rSTC-1 (1 μg/ml) markedly reduced the overall area of endothelial networks (FIG. 3B) and the structures that did form were discontinuous and poorly formed. Heat denaturation abrogated the effects of rSTC-1 (FIG. 3C).

Figure 4:
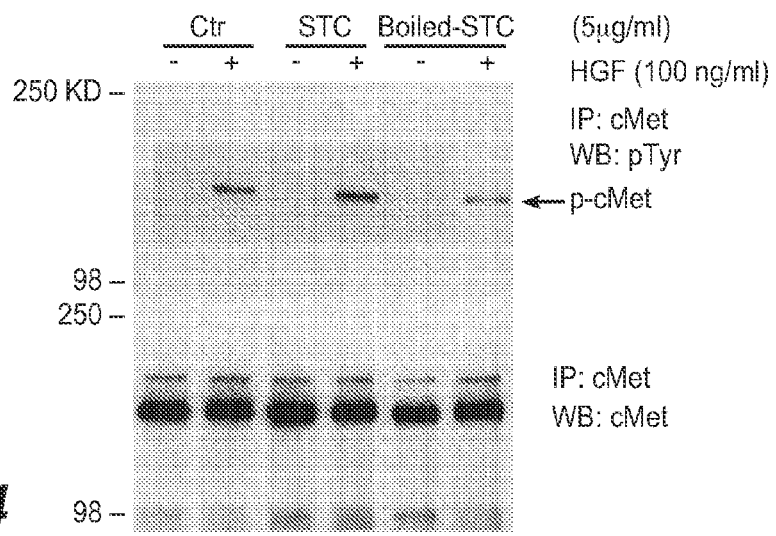
FIG. 4. STC-1 does not inhibit HGF induced c-met phosphorylation. HUVEC were pretreated for 30 min with 5 μg/ml STC-1 or 5 μg/ml boiled STC-1, then challenged with HGF (100 ng/ml) for 15 min. Lysates were subjected to immunoprecipitation for c-met, separated by gel electrophoresis, and transferred to nitrocellulose. The resulting blots were immunoblotted with antibodies to phosphotyrosine (pTyr)(top) or c-met (bottom).

Effects of STC-1 on HGF induced c-met phosphorylation. HGF induced the phosphorylation of c-met (FIG. 4). Pretreatment or cotreatment of HUVEC with 5 μg/ml STC-1 did not reduce the phosphorylation response of c-met to added HGF (FIG. 4), suggesting that STC-1 did not inhibit HGF binding to its receptor. To determine possible effects downstream of c-met phosphorylation, the effects of STC-1 on HGF-induced FAK activation was also examined. The data indicated that maximal FAK phosphorylation by HGF in HUVEC occurred at 60 min (data not shown). Pretreatment of the endothelial cells with STC-1 abrogated HGF-induced phosphorylation of FAK (data not shown). Although difficult to detect, the modest FAK phosphorylation induced by bFGF or VEGF (data not shown) was not inhibited by pretreatment with STC-1.

Figure 5A:
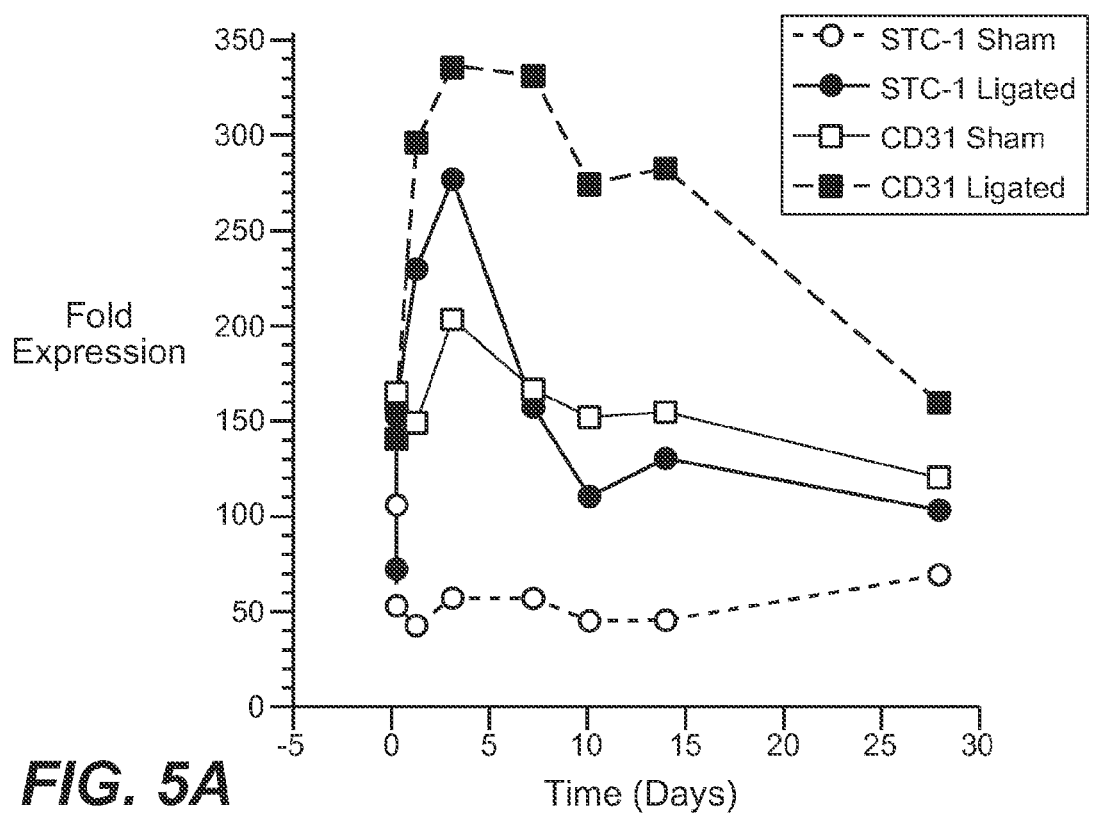
FIGS. 5A-B. STC-1 is unregulated in the hind limb ischemia model of angiogenesis.
Figure 5B:
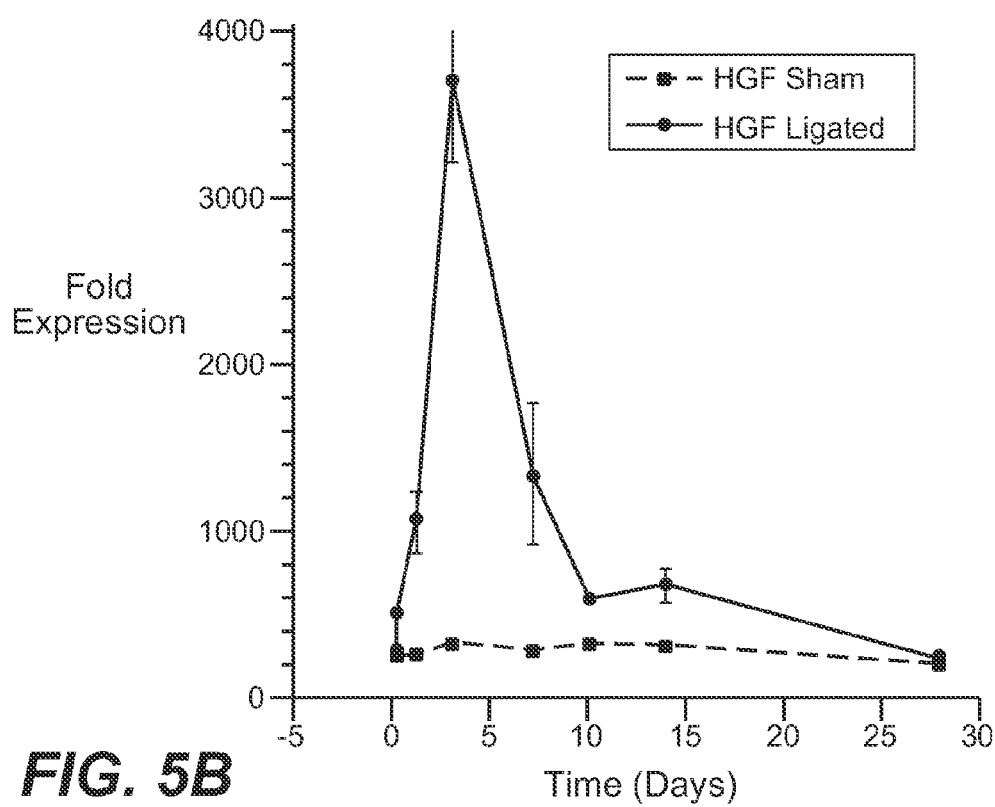

Expression of STC-1 in the hind-limb ischemia model of angiogenesis. We also evaluated the expression of STC-1 in the mouse femoral ligation assay. In this model, the femoral artery is ligated, dramatically reducing blood flow to the lower limb including the gastrocnemius muscle (7). This hypoxic insult results in the rapid development of new vessels in the hypoxic muscle as a component of the spontaneous recovery of perfusion which is also associated with proximal arteriogenesis (8,9). Because the newly developing vessels are not readily visualized in this assay, we also measured the mRNA levels of the endothelial marker, CD31 as an index of new vessel formation. As shown in FIG. 5A, both CD31 mRNA and STC-1 mRNA expression peaked at day 3 and then returned to lower levels at later time points. We also measured the mRNA levels of HGF. Interestingly, the expression of HGF also increased markedly in this in vivo model, peaking at day 3 (FIG. 5B)

Discussion

Stanniocalcin 1, a secreted protein, was first identified in fish, where it has been shown to regulate calcium and phosphate homeostasis (10,11). A unique feature of stanniocalcin 1 is its lack of homology to any other proteins, other than stanniocalcin 2 to which it is 34% identical at the amino acid level. The human homolog of stanniocalcin 1 is 73% homologous to the salmon protein. However, in contrast to the fish, where stanniocalcin 1 is exclusively localized to the organ of Stannius, the mammalian homolog exhibits a much broader expression profile. The function of the mammalian stanniocalcin 1 is generally poorly understood, although roles in calcium and phosphate homeostasis (12-14) and ovarian function (15) have been suggested. The majority of "functions" that have been attributed to mammalian stanniocalcin 1 are associative, i.e. they have been based on expression data or cellular localization. The data described herein provide the first "biological activity" of stanniocalcin 1 on mammalian cells. The activities in the Matrigel and migration assay, which are well accepted in the art as models for the multi-staged angiogeneis process, provide unexpected and important evidence for a role for stanniocalcin vascularization and angiogeneis-associated signaling and function.

We first identified stanniocalcin 1 as one of the genes that demonstrated marked upregulation in endothelial cells undergoing tubulogenesis (6), suggesting a possible role in angiogenesis. In situ studies demonstrated that the expression of stanniocalcin 1 was highly focal—high levels of expression were observed in small to large vessels at the periphery of lung and colon carcinomas and inflamed appendix (2,6). Moreover, STC-1 mRNA was markedly increased in rat corneas implanted with hydron pellets containing VEGF compared to vehicle controls (2). Examination of the phenotype of stanniocalcin 1 transgenic (Tg) mice (using a muscle specific promoter) revealed that the stanniocalcin 1 Tg mice were smaller than their wild type littermates, yet baseline organ vascularity as well as induction of increased vascular density following femoral ligation were enhanced (14). We herein report the surprising observation that stanniocalcin-1 is an autocrine modulator of HGF-induced endothelial migration and morphogenesis (cord formation). These effects were selective to particular angiogenic factors, in particular HGF, because the responses of endothelial cells to either VEGF or bFGF were not modulated in these in these assays. Of the growth factors and cytokines examined, HGF was the most potent inducer of stanniocalcin 1 secretion. In vivo data provide further support for this conclusion. In an in vivo model of physiological angiogenesis, the mouse femoral ligation model, the expression profile of stanniocalcin 1 mRNA was similar to that of the endothelial marker CD31, and moreover, the peak expression of stanniocalcin 1 mRNA was preceded by peak expression of HGF.

The mechanism of the selective inhibition of the angiogenic action of a first angiogenic factor but not of a second angiogenic factor on endothelial cells is intriguing—stanniocalcin did not inhibit HGF induced endothelial proliferation or c-met phosphorylation, ruling out a direct inhibitory effect on HGF binding to its receptor. However, the selective inhibitory effects of STC-1 on HGF mediated responses (versus bFGF or VEGF) strongly suggest that STC-1 modulates specific features of HGF signaling, and thus its angiogenic effector pathway. STC-1 reduced HGF-induced FAK phosphorylation, consistent with the notion that STC-1 interferes with one or more downstream signaling pathways activated by the c-met receptor. Morever, the effects of STC-1 appears to be selective for HGF since bFGF and VEGF-induced FAK phosphorylation is not inhibited. FAK is a focal adhesion kinase that is localized in focal adhesions and has been shown to play an important role in integrin-mediated cellular functions; FAK activation is also linked to HGF-induced cell motility. The data described herein are consistent with a modulator role of STC-1 in angiogenesis, possibly serving as a "Stop signal" or stabilization factor contributing to the maturation of newly formed blood vessels. Although HGF is not a selective endothelial mitogen or motogen, it is a very potent angiogenic/growth agent (16,17) and the expression of both HGF and its receptor c-met are known to be upregulated in both physiological (18,19) and pathological angiogenesis (20,21). Therefore, as described herein, STC-1 provides a unique and potentially highly advantageous target for selective therapeutic modulation of angiogenesis. In one aspect, it is an advantageous target for selective modulation of certain, but not all, steps in the multi-stage angiogenic process.

STC-1 receptors, at least in the liver and kidney, have been reported to be present both on the plasma membrane and in the mitochondria (22). Furthermore, despite being a secreted protein, STC-1 is sequestered in the mitochondria (22) and has been proposed to play a role in the regulation of cellular metabolism (14,22). Thus the elevated expression of STC-1 during angiogenesis may play additional roles in the metabolic requirements of endothelial cells and other cells involved in the formation of new blood vessels.

REFERENCES

1. Xin, X., Yang, S., Ingle, G., Zlot, C., Rangell, L., Kowalski, J., Schwall, R., Ferrara, N., and Gerritsen, M. (2001) *Am J Pathol*, 1111-1120
2. Gerritsen, M. E., Soriano, R., Yang, S., Ingle, G., Zlot, C., Toy, K., Winer, J., Draksharapu, A., Peale, F., Wu, T. D., and Williams, P. M. (2002) *Physiol Genomics* 10(1), 13-20.
3. Hongo, J., Mora-Worms, M., Lucas, C., and Fendly, B. (1995) *Hybridoma* 14, 253-259
4. Kohler, G., and Milstein, C. (1975) *Nature* 256, 495-497
5. Freund, Y., and Blair, P. (1982) *J Immunol* 129, 2826-2830
6. Kahn, J., Mehraban, F., Ingle, G., Xin, X., Bryant, J., Vehar, G., Schoenfeld, J., Grimaldi, C., Peale, F., Drakharapu, A., Lewin, D., and Gerritsen, M. (2000) *Am J Pathol* 156, 1887-1900
7. Couffinhal, T., Silver, M., Zheng, L. P., Kearney, M., Witzenbichler, B., and Isner, J. M. (1998) *Am J Pathol* 152(6), 1667-79.
8. Ito, W. D., Arras, M., Scholz, D., Winkler, B., Htun, P., and Schaper, W. (1997) *Am J Physiol* 273(3 Pt 2), H1255-65.
9. Scholz, D., Ito, W., Fleming, I., Deindl, E., Sauer, A., Wiesnet, M., Busse, R., Schaper, J., and Schaper, W. (2000) *Virchows Arch* 436(3), 257-70.
10. Wagner, G., Hampong, M., Park, C., and Copp, D. (1986) *Gen Comp Endocrinol* 63, 481-491
11. Wagner, G. F., Dimattia, G. E., Davie, J. R., Copp, D. H., and Friesen, H. G. (1992) *Mol Cell Endocrinol* 90(1), 7-15
12. Wagner, G. F., Vozzolo, B. L., Jaworski, E., Haddad, M., Kline, R. L., Olsen, H. S., Rosen, C. A., Davidson, M. B., and Renfro, J. L. (1997) *J Bone Miner Res* 12(2), 165-71
13. Varghese, R., Gagliardi, A., Bialek, P., Yee, S., Wagner, G., and Dimattia, G. (2002) *Endocrinology* 143, 868-876
14. Filvaroff, E. H., Guillet, S., Zlot, C., Bao, M., Ingle, G., Steinmetz, H., Hoeffel, J., Bunting, S., Ross, J., Carano, R. A., Powell-Braxton, L., Wagner, G. F., Eckert, R., Gerritsen, M. E., and French, D. M. (2002) *Endocrinology* 143 (9), 3681-90.
15. Paciga, M., A J, W., Dimattia, G., and Wagner, G. (2002) *Endocrinology* 143, 3925-2934
16. Morishita, R., Aoki, M., Yo, Y., and Ogihara, I. (2002) *Endocr. J.* 29, 273-284
17. Bussolino, F., Di Renzo, M. F., Ziche, M., Bocchietto, E., Olivero, M., Naldini, L., Gaudino, G., Tamagnone, L., Coffer, A., and Comoglio, P. M. (1992) *J Cell Biol* 119(3), 629-41
18. Hayashi, S., Morishita, R., Nakamura, S., Yamamoto, K., Moriguchi, A., Nagano, T., Taiji, M., Noguchi, H., Matsumoto, K., Nakamura, T., Higaki, J., and Ogihara, T. (1999) *Circulation* 100(19 Suppl), 11301-8
19. Jennische, E., Ekberg, S., and Matejka, G. L. (1993) Am J Physiol 265(1 Pt 1), C122-8
20. Schmidt, N. O., Westphal, M., Hagel, C., Ergun, S., Stavrou, D., Rosen, E. M., and Lamszus, K. (1999) *Int J Cancer* 84(1), 10-8
21. To, C. T., and Tsao, M. S. (1998) Oncol *Rep* 5(5), 1013-24
22. McCudden, C., James, K., Hasilo, C., and Wagner, G. (2002) J Biol Chem 277, 45249-45258

The invention claimed is:

1. A monoclonal antibody that specifically binds to stanniocalcin and that comprises all of the complementarity determining regions (CDRs) of a heavy chain and all of the complementarity determining regions (CDRs) of a light chain from an antibody produced by a hybridoma selected from the group consisting of:

3E10.1F5.1D11 (ATCC Deposit No. PTA-5100); 2F4.2F11.1H12 (ATCC Deposit No. PTA-5103); 1F10.2F12.1E7 (ATCC Deposit No. PTA-5101); 18F1.1E6.1B10 (ATCC Deposit No. PTA-5099); and 12C3.2F3.2D8 (ATCC Deposit No. PTA-5102).

2. The antibody of claim 1, further comprising a cytotoxic agent.

3. The antibody of claim 1, further comprising a detectable label.

4. A pharmaceutical composition comprising the antibody of claim 1 and a pharmaceutically acceptable carrier.

5. A hybridoma selected from the group consisting of:
3E10.1F5.1D11 (ATCC Deposit No. PTA-5100); 2F4.2F11.1H12 (ATCC Deposit No. PTA-5103); 1F10.2F12.1E7 (ATCC Deposit No. PTA-5101); 18F1.1E6.1B10 (ATCC Deposit No. PTA-5099); and 12C3.2F3.2D8 (ATCC Deposit No. PTA-5102).

6. A monoclonal antibody produced by a hybridoma selected from the group consisting of:
3E10.1F5.1D11 (ATCC Deposit No. PTA-5100); 2F4.2F11.1H12 (ATCC Deposit No. PTA-5103); 1F10.2F12.1E7 (ATCC Deposit No. PTA-5101); 18F1.1E6.1B10 (ATCC Deposit No. PTA-5099); and 12C3.2F3.2D8 (ATCC Deposit No. PTA-5102).

7. The antibody of claim 6, further comprising a cytotoxic agent.

8. The antibody of claim 6, further comprising a detectable label.

9. A pharmaceutical composition comprising the antibody of claim 6 and a pharmaceutically acceptable carrier.

* * * * *

SEQUENCE LISTING

<160> NUMBER OF SEQ ID NOS: 3

<210> SEQ ID NO 1
<211> LENGTH: 3901
<212> TYPE: DNA
<213> ORGANISM: Homo sapien

<400> SEQUENCE: 1

| | | | | | |
|---|---|---|---|---|---|
| cagtttgcaa | aagccagagg | tgcaagaagc | agcgactgca | gcagcagcag | 50 |
| cagcagcggc | ggtggcagca | gcagcagcag | cggcggcagc | agcagcagca | 100 |
| gcggaggcac | cggtggcagc | agcagcatca | ccagcaacaa | caacaaaaaa | 150 |
| aaatcctcat | caaatcctca | cctaagcttt | cagtgtatcc | agatccacat | 200 |
| cttcactcaa | gccaggagag | ggaaagagga | aggggggca | ggaaaaaaaa | 250 |
| aaacccaac | aacttagcgg | aaacttctca | gagaatgctc | caaaactcag | 300 |
| cagtgcttct | ggtgctggtg | atcagtgctt | ctgcaaccca | tgaggcggag | 350 |
| cagaatgact | ctgtgagccc | caggaaatcc | cgagtggcgg | ctcaaaactc | 400 |
| agctgaagtg | gttcgttgcc | tcaacagtgc | tctacaggtc | ggctgcgggg | 450 |
| cttttgcatg | cctggaaaac | tccacctgtg | acacagatgg | gatgtatgac | 500 |
| atctgtaaat | ccttcttgta | cagcgctgct | aaatttgaca | ctcagggaaa | 550 |
| agcattcgtc | aaagagagct | taaaatgcat | cgccaacggg | gtcacctcca | 600 |
| aggtcttcct | cgccattcgg | aggtgctcca | ctttccaaag | gatgattgct | 650 |
| gaggtgcagg | aagagtgcta | cagcaagctg | aatgtgtgca | gcatcgccaa | 700 |
| gcggaaccct | gaagccatca | ctgaggtcgt | ccagctgccc | aatcacttct | 750 |
| ccaacagata | ctataacaga | cttgtccgaa | gcctgctgga | atgtgatgaa | 800 |
| gacacagtca | gcacaatcag | agacagcctg | atggagaaaa | ttgggcctaa | 850 |
| catggccagc | ctcttccaca | tcctgcagac | agaccactgt | gcccaaacac | 900 |
| acccacgagc | tgacttcaac | aggagacgca | ccaatgagcc | gcagaagctg | 950 |
| aaagtcctcc | tcaggaacct | ccgaggtgag | gaggactctc | cctcccacat | 1000 |
| caaacgcaca | tcccatgaga | gtgcataacc | agggagaggt | tattcacaac | 1050 |
| ctcaccaaac | tagtatcatt | ttagggggtgt | tgacacacca | attttgagtg | 1100 |
| tactgtgcct | ggtttgattt | ttttaaagta | gttcctattt | tctatccccc | 1150 |
| ttaaagaaaa | ttgcatgaaa | ctaggcttct | gtaatcaata | tcccaacatt | 1200 |
| ctgcaatggc | agcattccca | ccaacaaaat | ccatgtgatc | attctgcctc | 1250 |
| tcctcaggag | aaagtaccct | cttttaccaa | cttcctctgc | catgtctttt | 1300 |
| cccctgctcc | cctgagacca | cccccaaaca | caaaacattc | atgtaactct | 1350 |
| ccagccattg | taatttgaag | atgtggatcc | ctttagaacg | gttgcccag | 1400 |
| tagagttagc | tgataaggaa | actttattta | aatgcatgtc | ttaaatgctc | 1450 |
| ataaagatgt | taaatggaat | tcgtgttatg | aatctgtgct | ggccatggac | 1500 |
| gaatatgaat | gtcacatttg | aattcttgat | ctctaatgag | ctagtgtctt | 1550 |
| atggtcttga | tcctccaatg | tctaattttc | tttccgacac | atttaccaaa | 1600 |
| ttgcttgagc | ctggctgtcc | aaccagactt | tgagcctgca | tcttcttgca | 1650 |
| tctaatgaaa | aacaaaaagc | taacatcttt | acgtactgta | actgctcaga | 1700 |

| | |
|---|---|
| gctttaaaag tatctttaac aattgtctta aaaccagaga atcttaaggt | 1750 |
| ctaactgtgg aatataaata gctgaaaact aatgtactgt acataaattc | 1800 |
| cagaggactc tgcttaaaca aagcagtata taataacttt attgcatata | 1850 |
| gatttagttt tgtaacttag ctttattttt cttttcctgg gaatggaata | 1900 |
| actatctcac ttccagatat ccacataaat gctccttgtg cctttttta | 1950 |
| taactaaggg ggtagaagta gttttaattc aacatcaaaa cttaagatgg | 2000 |
| gcctgtatga gacaggaaaa accaacaggt ttatctgaag gaccccaggt | 2050 |
| aagatgttaa tctcccagcc cacctcaacc cagaggctac tcttgactta | 2100 |
| gacctatact gaaagatctc tgtcacatcc aactggaaat tccaggaacc | 2150 |
| aaaaagagca tccctatggg cttggaccac ttacagtgtg ataaggccta | 2200 |
| ctatacatta ggaagtggta gttctttact cgtccccttt catcggtgcc | 2250 |
| tggtactctg gcaaatgatg atggggtggg agactttcca ttaaatcaat | 2300 |
| caggaatgag tcaatcagcc tttaggtctt tagtccgggg gacttggggc | 2350 |
| tgagagagta taaataaccc tgggctgtcc agccttaata gacttctctt | 2400 |
| acattttcgt cctgtagcac gctgcctgcc aaagtagtcc tggcagctgg | 2450 |
| accatctctg taggatcgta aaaaaataga aaaaagaaa aaaaaagaa | 2500 |
| agaaagaggg aaaaagagct ggtggtttga tcatttctgc catgatgttt | 2550 |
| acaagatggc gaccaccaaa gtcaaacgac taacctatct atgaacaaca | 2600 |
| gtagtttctc agggtcactg tccttgaacc caacagtccc ttatgagcgt | 2650 |
| cactgcccac caaaggtcaa tgtcaagaga ggaagagagg gaggaggggt | 2700 |
| aggactgcag gggccactcc aaactcgctt aggtagaaac tattggtgct | 2750 |
| cgactctcac taggctaaac tcaagatttg accaaatcga gtgataggga | 2800 |
| tcctggtggg aggagagagg gcacatctcc agaaaatga aaagcaatac | 2850 |
| aactttacca taaagccttt aaaaccagta acgtgctgct caaggaccaa | 2900 |
| gagcaattgc agcagaccca gcagcagcag cagcagcaca aacattgctg | 2950 |
| cctttgtccc cacacagcct ctaagcgtgc tgacatcaga ttgttaaggg | 3000 |
| cattttata ctcagaactg tcccatcccc aggtccccaa acttatggac | 3050 |
| actgccttag cctcttggaa atcaggtaga ccatattcta agttagactc | 3100 |
| ttcccctccc tcccacactt cccaccccca ggcaaggctg acttctctga | 3150 |
| atcagaaaag ctattaaagt ttgtgtgttg tgtccatttt gcaaacccaa | 3200 |
| ctaagccagg accccaatgc gacaagtagt tcatgagtat tcctagcaaa | 3250 |
| tttctctctt tcttcagttc agtagatttc cttttttctt ttcttttttt | 3300 |
| ttttttttt tttttggctg tgacctcttc aaaccgtggt accccccctt | 3350 |
| ttctccccac gatgatatct atatatgtat ctacaataca tatatctaca | 3400 |
| catacagaaa gaagcagttc tcacatgttg ctagtttttt gcttctcttt | 3450 |
| cccccaccct actccctcca attccccct taaacttcca aagcttcgtc | 3500 |
| ttgtgtttgc tgcagagtga ttcgggggct gacctagacc agtttgcatg | 3550 |
| attcttctct tgtgatttgg ttgcacttta gacatttttg tgccattata | 3600 |
| tttgcattat gtatttataa tttaaatgat atttaggttt ttggctgagt | 3650 |

```
actggaataa acagtgagca tatctggtat atgtcattat ttattgttaa       3700
attacatttt ttaagctcca tgtgcatata aaggttatga aacatatcat       3750
ggtaatgaca gatgcaagtt attttatttg cttatttttt ataattaaag       3800
atgccatagc ataatatgaa gcctttggtg aattccttct aagataaaaa       3850
taataataaa gtgttacgtt ttattggttt caaaaaaaaa aaaaaaaaaa       3900
a                                                             3901
```

<210> SEQ ID NO 2
<211> LENGTH: 247
<212> TYPE: PRT
<213> ORGANISM: Homo sapien

<400> SEQUENCE: 2

```
Met Leu Gln Asn Ser Ala Val Leu Val Leu Val Ile Ser Ala
  1               5                  10                  15

Ser Ala Thr His Glu Ala Glu Gln Asn Asp Ser Val Ser Pro Arg
                 20                  25                  30

Lys Ser Arg Val Ala Ala Gln Asn Ser Ala Glu Val Val Arg Cys
             35                  40                  45

Leu Asn Ser Ala Leu Gln Val Gly Cys Gly Ala Phe Ala Cys Leu
         50                  55                  60

Glu Asn Ser Thr Cys Asp Thr Asp Gly Met Tyr Asp Ile Cys Lys
 65                  70                                  75

Ser Phe Leu Tyr Ser Ala Ala Lys Phe Asp Thr Gln Gly Lys Ala
             80                  85                  90

Phe Val Lys Glu Ser Leu Lys Cys Ile Ala Asn Gly Val Thr Ser
             95                 100                 105

Lys Val Phe Leu Ala Ile Arg Arg Cys Ser Thr Phe Gln Arg Met
            110                 115                 120

Ile Ala Glu Val Gln Glu Glu Cys Tyr Ser Lys Leu Asn Val Cys
            125                 130                 135

Ser Ile Ala Lys Arg Asn Pro Glu Ala Ile Thr Glu Val Val Gln
            140                 145                 150

Leu Pro Asn His Phe Ser Asn Arg Tyr Tyr Asn Arg Leu Val Arg
            155                 160                 165

Ser Leu Leu Glu Cys Asp Glu Asp Thr Val Ser Thr Ile Arg Asp
            170                 175                 180

Ser Leu Met Glu Lys Ile Gly Pro Asn Met Ala Ser Leu Phe His
            185                 190                 195

Ile Leu Gln Thr Asp His Cys Ala Gln Thr His Pro Arg Ala Asp
            200                 205                 210

Phe Asn Arg Arg Arg Thr Asn Glu Pro Gln Lys Leu Lys Val Leu
            215                 220                 225

Leu Arg Asn Leu Arg Gly Glu Glu Asp Ser Pro Ser His Ile Lys
            230                 235                 240

Arg Thr Ser His Glu Ser Ala
            245
```

<210> SEQ ID NO 3
<211> LENGTH: 20
<212> TYPE: PRT
<213> ORGANISM: Homo sapien

<400> SEQUENCE: 3

```
-continued

Cys Tyr Asn Arg Leu Val Arg Ser Leu Leu Glu Ala Asp Glu Asp
 1               5                  10                  15

Thr Val Ser Thr Ile
                20
```